(12) United States Patent
Melki et al.

(10) Patent No.: US 12,642,504 B2
(45) Date of Patent: Jun. 2, 2026

(54) SYSTEMS AND METHODS FOR ELECTROMECHANICAL WAVE IMAGING WITH MACHINE LEARNING FOR AUTOMATED ACTIVATION MAP GENERATION FOR DISPLAY ON AN IMAGE PROCESSING UNIT

(71) Applicant: THE TRUSTEES OF COLUMBIA UNIVERSITY IN THE CITY OF NEW YORK, New York, NY (US)

(72) Inventors: Lea Melki, New York, NY (US); Elisa Konofagou, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 312 days.

(21) Appl. No.: 18/191,813

(22) Filed: Mar. 28, 2023

(65) Prior Publication Data

US 2023/0363736 A1 Nov. 16, 2023

Related U.S. Application Data

(63) Continuation-in-part of application No. PCT/US2021/052395, filed on Sep. 28, 2021.

(60) Provisional application No. 63/085,654, filed on Sep. 30, 2020, provisional application No. 63/084,393, filed on Sep. 28, 2020.

(51) Int. Cl.
| | |
|---|---|
| *A61B 8/00* | (2006.01) |
| *A61B 5/00* | (2006.01) |
| *A61B 8/08* | (2006.01) |
| *G06T 3/02* | (2024.01) |

(52) U.S. Cl.
CPC .......... *A61B 8/4483* (2013.01); *A61B 5/7267* (2013.01); *A61B 8/0858* (2013.01); *G06T 3/02* (2024.01)

(58) Field of Classification Search
None
See application file for complete search history.

(56) References Cited

U.S. PATENT DOCUMENTS

| | | | |
|---|---|---|---|
| 6,799,064 | B1 | 9/2004 | Hassett |
| 7,187,964 | B2 | 3/2007 | Khoury |
| 7,211,045 | B2 | 5/2007 | Dala-Krish et al. |
| 7,751,882 | B1 | 7/2010 | Helland |
| 7,787,951 | B1 | 8/2010 | Min |
| 8,165,666 | B1 | 4/2012 | Briggs et al. |

(Continued)

OTHER PUBLICATIONS

Costet et al., "Electromechanical Wave Imaging (EWI) validation in all four cardiac chambers with 3D electroanatomic mapping in canines in vivo," Phys Med Biol, 61(22), 8105-8119 (2016).

(Continued)

*Primary Examiner* — Haris Sabah
(74) *Attorney, Agent, or Firm* — Baker Botts L.L.P.

(57) ABSTRACT

The present subject matter relates to techniques for electromechanical wave imaging. The disclosed system can include a processor that can be configured to perform an automated selection of at least one zero-crossing location using a heuristic-based baseline and/or a machine learning classifier and generate an electromechanical wave imaging isochrone based on the automated selection.

19 Claims, 21 Drawing Sheets
(12 of 21 Drawing Sheet(s) Filed in Color)

Ground truth – manual ZCs

Heuristic-based automated approach – first ZCs

Heuristic-based automated approach – conditions on negative peak amplitude and slope steepness at ZC

(56) References Cited

U.S. PATENT DOCUMENTS

| | | | |
|---|---|---|---|
| 8,326,419 B2 | 12/2012 | Rosenberg et al. | |
| 9,687,204 B2 * | 6/2017 | Mountney | A61B 8/4245 |
| 2011/0208038 A1 | 8/2011 | Konofagou et al. | |
| 2012/0283587 A1 | 11/2012 | Gosh et al. | |
| 2013/0072773 A1 | 3/2013 | Wu et al. | |
| 2014/0343424 A1 | 11/2014 | Konofagou et al. | |
| 2016/0249880 A1 | 9/2016 | Konofagou et al. | |
| 2016/0358099 A1 | 12/2016 | Sturlaugson et al. | |
| 2016/0379667 A1 | 12/2016 | Zhang et al. | |
| 2017/0231521 A1 | 8/2017 | Axelrod | |
| 2019/0148011 A1 * | 5/2019 | Rao | G16H 50/20 |
| | | | 600/437 |
| 2019/0261949 A1 * | 8/2019 | Labyed | A61B 8/5223 |
| 2020/0064469 A1 * | 2/2020 | Trahey | G06N 5/046 |
| 2020/0214662 A1 * | 7/2020 | Konofagou | A61B 8/4416 |

OTHER PUBLICATIONS

Costet et al., "Non-invasive Characterization of Focal Arrhythmia with Electromechanical Wave Imaging in Vivo," Ultrasound Med Biol., 44(11), 2241-2249 (2018).

Grace et al., "Dipole Density Mapping of Atrial Fibrillation," Eur Heart J., 38(1): 5-9 (2017).

Grubb et al., "Noninvasive localization of cardiac arrhythmias using electromechanical wave imaging," Sci Trans Med., 12(536) (2020).

International Search Report and Written Opinion mailed Dec. 22, 2021 in International Application No. PCT/US2021/052395.

Jan et al., "Intra-cardiac ultrasound guided approach for catheter ablation of typical right free wall accessory pathways," BMC Cardiovasc Disord., 20(1):210 (2020).

Liu et al., "Noninvasive mapping of transmural potentials during activation in swine hearts from body surface electrocardiograms," IEEE Trans Med Imaging., 31(9) 1777-1785 (2012).

Melki et al., "3D-rendered Electromechanical Wave Imaging for Localization of Accessory Pathways in Wolff-Parkinson-White Minors," Annu Int Conf IEEE Eng Med Biol Soc., 6192-6195 (2019).

Olafsson et al., "Cardiac activation mapping using ultrasound current source density imaging (UCSDI)," IEEE Trans Ultrason Ferroelectr Freq Control., 56(3), 565-574 (2009).

O'Shea et al., "ElectroMap: High-throughput open-source software for analysis and mapping of cardiac electrophysiology," Sci Rep., 9: 1389 (2019).

Prakosa et al., "Cardiac electrophysiological activation pattern estimation from images using a patient-specific database of synthetic image sequences," IEEE Transactions on Biomedical Engineering, 61.2, 235-245 (2013).

* cited by examiner

MACHINE LEARNING-BASED f) Random forest

POST   LV

MACHINE LEARNING-BASED e) SVM

POST   LV

MACHINE LEARNING-BASED d) Logistic regression

POST   LV

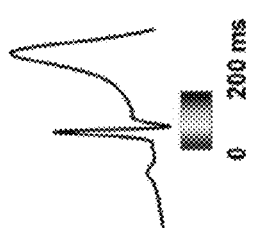
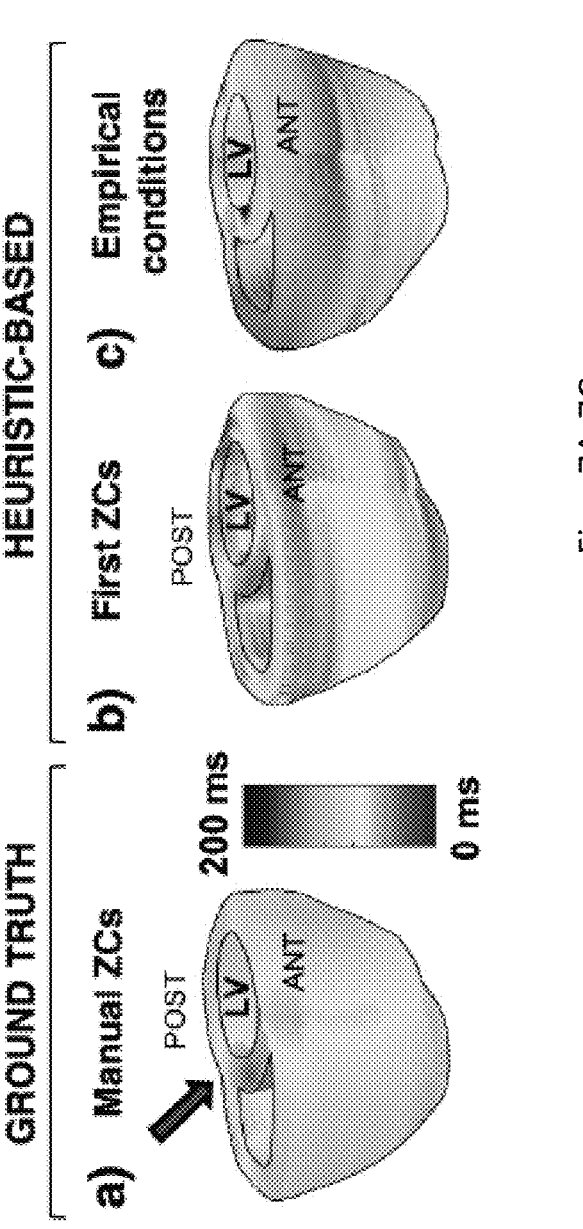
Figs. 7A-7C

SYSTEMS AND METHODS FOR ELECTROMECHANICAL WAVE IMAGING WITH MACHINE LEARNING FOR AUTOMATED ACTIVATION MAP GENERATION FOR DISPLAY ON AN IMAGE PROCESSING UNIT

CROSS-REFERENCE TO RELATED APPLICATION

This application is a continuation in part of International Patent Application No. PCT/US2021/052395, which claims priority to U.S. Provisional Patent Application Nos. 63/084, 393, which was filed on Sep. 28, 2020, and 63/085,654, which was filed on Sep. 30, 2020, the entire contents of which are incorporated by reference herein.

GRANT INFORMATION

This invention was made with government support under grant number HL-140646-01 awarded by the National Institutes of Health (NIH). The government has certain rights in the invention.

BACKGROUND

Early detection of cardiac conduction malfunctions such as arrhythmias can be helpful for treating cardiovascular disease. Certain imaging techniques for cardiac activation sequence mapping are invasive, ionizing, time-consuming and expensive. Echocardiography-based imaging techniques can be low-cost, non-invasive, and do not require the use of potentially harmful ionizing radiation. For example, electromechanical wave imaging (EWI) can be a high frame-rate ultrasound-based functional modality that can non-invasively map the electromechanical activation of the heart. However, manual selection of the zero-crossing (ZC) locations on the incremental axial strain curves for EWI isochrone generation EWI can be time-consuming, in particular, with large patient populations.

Therefore, there is a need for an improved non-invasive imaging ultrasound technique, which can be used for the early diagnosis of cardiovascular disease.

SUMMARY

The disclosed subject matter provides techniques for electromechanical wave imaging (EWI) with automated activation map generation.

An example system can include a processor configured to receive a dataset, perform an automated selection of at least one zero-crossing location on the dataset using a heuristic-based baseline and/or a machine learning classifier and generate an electromechanical wave imaging isochrone based on the automated selection.

In certain embodiments, the machine learning classifier can be a logistic regression classifier, a support vector machine classifier, or a Random Forest classifier. In non-limiting embodiments, the machine learning classifier can be a Random Forest classifier.

The Random Forest classifier can be configured to have a precision rate of more than about 89.5%. In some embodiments, the Random Forest classifier can include at least about 200 estimators.

In certain embodiments, the processor can be configured to collect a plurality of features from a dataset. The plurality of features can include a spatial coordinate, a positive to negative zero-crossing time-point, a slope of a strain curve at each zero-crossing location, a maximum positive strain value surrounding each zero-crossing location, a minimum negative strain value surrounding each zero-crossing location, a time-point location of the maximum and the minimum strain values, or combinations thereof.

In certain embodiments, the machine learning classifier can be trained with ground truth samples. The ground truth samples can be manually generated isochrones.

In certain embodiments, the machine learning classifier can be trained to select the at least one zero-crossing by selecting a zero-crossing location with a highest probability for each pixel or selecting a zero-cross location that has a probability higher than a cutoff threshold. The cutoff threshold can be determined based on a sensitivity and/or true positive value of a dataset.

In certain embodiments, the processor is configured to receive an external data set and perform the automated selection based on the external data set.

In certain embodiments, the system can further include a transducer configured to perform electromechanical wave imaging. In non-limiting embodiments, the processor can perform beamforming on an image acquired by the transducer, estimate the displacement of the tissue based on the image, and generate an incremental strain curve based on the displacement.

In certain embodiments, the dataset can include electromechanical wave images, electromechanical wave imaging strain curves, or a combination thereof.

The disclosed subject matter provides methods for electromechanical wave imaging of a tissue of a subject. An example method can include receiving a dataset, performing an automated selection of at least one zero-crossing location on the dataset using a heuristic-based baseline and/or a machine learning classifier and generating an electromechanical wave imaging isochrone based on the automated selection.

In certain embodiments, the method can include collecting a plurality of features from a dataset. The plurality of features can include a spatial coordinate, a positive to negative zero-crossing time-point, a slope of a strain curve at each zero-crossing location, a maximum positive strain value surrounding each zero-crossing location, a minimum negative strain value surrounding each zero-crossing location, a time-point location of the maximum and the minimum strain values, or combinations thereof.

In certain embodiments, the method can further include training the machine learning classifier with ground truth samples. The ground truth samples can be manually generated isochrones.

In certain embodiments, the machine learning classifier can be trained to select the at least one zero-crossing by selecting a zero-crossing location with a highest probability for each pixel or selecting a zero-cross location that has a probability higher than a cutoff threshold. The cutoff threshold can be determined based on a sensitivity and/or true positive value of a dataset.

In certain embodiments, the method can further include receiving an external data set and performing the automated selection using the external data set.

In certain embodiments, the subject can be a Wolff-Parkinson-White patient an atrial flutter patient, or a ventricular trachyacardia patient.

The disclosed subject matter will be further described below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 7A-7F provide diagrams showing 3D-rendered isochrones generated with different automated approaches on the example of a patient in sinus rhythm taken from the human testing dataset compared to the manually generated isochrone: 7A) Manual ground truth, 7B) Naive heuristic-based automated approach selecting the first occurring ZCs, 7C) Rule-based heuristic automated approach selecting the ZCs satisfying pre-determined conditions, 7D) ML model with logistic regression classifier, 7E) ML model with SVM classifier, and 7F) ML model with Random Forest classifier in accordance with the disclosed subject matter.

Figure 1:
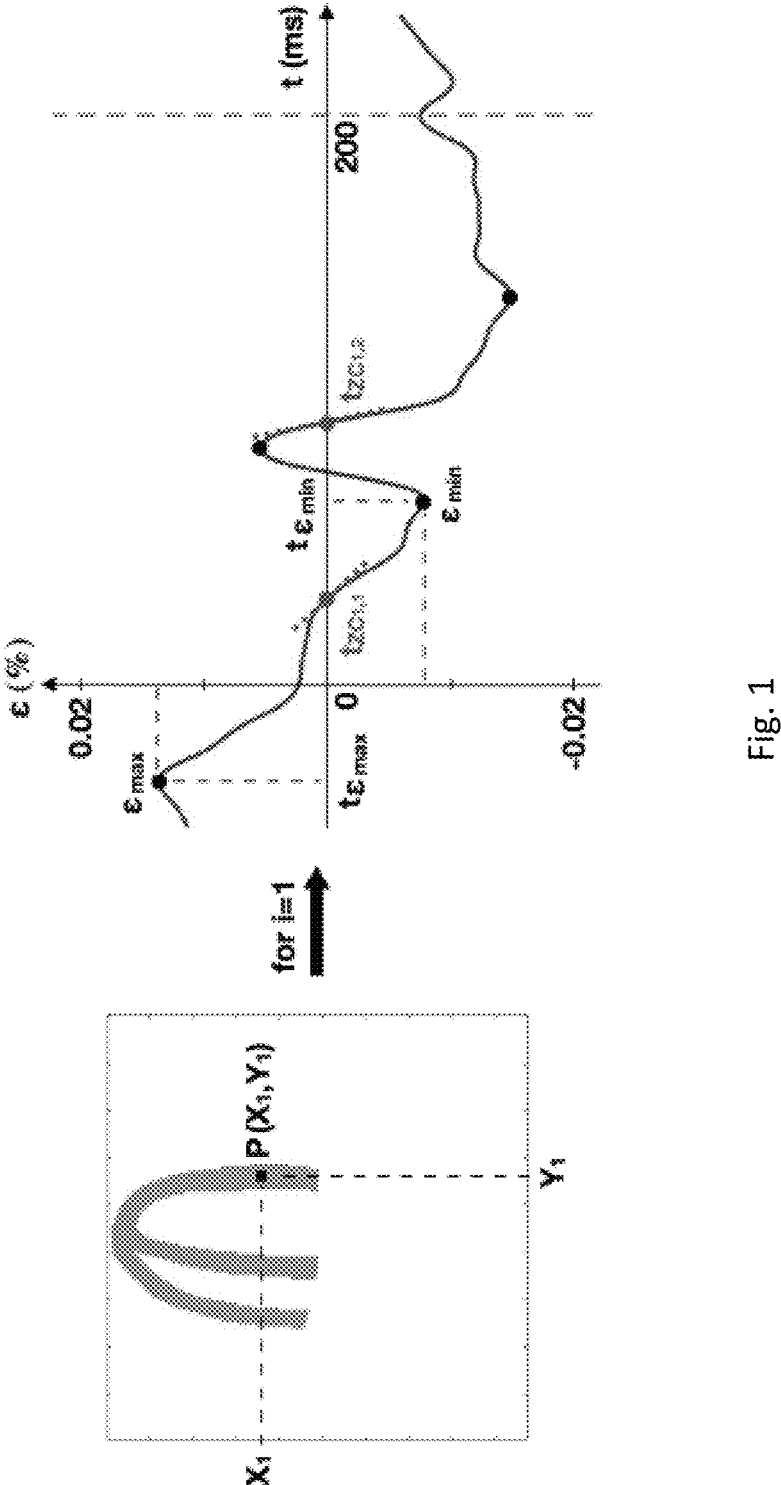
FIG. 1 provides graphs showing an incremental strain curve and feature collections in an apical four-chamber view ventricular mask in accordance with the disclosed subject matter.

It is to be understood that both the foregoing general description and the following detailed description are exemplary and are intended to provide further explanation of the disclosed subject matter.

DETAILED DESCRIPTION

The disclosed subject matter provides techniques for electromechanical wave imaging (EWI) with automated activation map generation. The disclosed system provides systems and methods for EWI activation map generation with machine learning.

The terms "comprise(s)," "include(s)," "having," "has," "can," "contain(s)," and variants thereof, as used herein, are intended to be open-ended transitional phrases, terms, or words that do not preclude additional acts or structures. The singular forms "a," "an," and "the" include plural references unless the context clearly dictates otherwise. The present disclosure also contemplates other embodiments "comprising," "consisting of," and "consisting essentially of," the embodiments or elements presented herein, whether explicitly set forth or not.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 10%, up to 5%, and up to 1% of a given value. Alternatively, e.g., with respect to biological systems or processes, the term can mean within an order of magnitude, within 5-fold, and within 2-fold, of a value.

The term "coupled," as used herein, refers to the connection of a device component to another device component by methods known in the art.

As used herein, the term "subject" includes any human or nonhuman animal. The term "nonhuman animal" includes, but is not limited to, all vertebrates, e.g., mammals and non-mammals, such as nonhuman primates, dogs, cats, sheep, horses, cows, chickens, amphibians, reptiles, etc.

In certain embodiments, the disclosed subject matter provides a system for electromechanical wave imaging (EWI) of a tissue of a subject. An example system can include a processor. The processor can be configured to perform the instructions specified by software stored in a hard drive, a removable storage medium, or any other storage media. The software can include computer codes, which can be written in a variety of languages, e.g., MAT- LAB and/or Microsoft Visual C++. Additionally or alternatively, the processor can include hardware logic, such as logic implemented in an application-specific integrated circuit (ASIC). The processor can be configured to control one or more of the system components. For example, and as embodied herein, the processor can be configured to control the operation of the transducer.

In certain embodiments, the processor can be configured to perform an automated selection of at least one zero-crossing (ZC) location. In non-limiting embodiments, the processor can be configured to perform the automated selection using a machine learning classifier. The machine learning classifier can be a logistic regression classifier, a support vector machine (SVM) classifier, a convolutional neuronal network (CNN) classifier, a recurrent neuronal network (RNN) classifier, or a Random Forest classifier. In some embodiments, the machine learning classifier can be a Random Forest classifier, which can include at least about 10, about 20, about 30, about 40, about 50, about 100, about 150, about 200, about 300, about 400, or about 500 estimators. In non-limiting embodiments, the machine learning classifier can be configured to have a precision rate of more than about 60%, about 70%, about 80%, about 89.5%, about 90%, or about 95%.

In certain embodiments, the processor can be configured to collect a plurality of features from a dataset. The features can include a spatial coordinate, a positive to negative zero-crossing time-point, a slope of a strain curve at each zero-crossing location, a maximum positive strain value surrounding each zero-crossing location, a minimum negative strain value surrounding each zero-crossing location, a time-point location of the maximum and the minimum strain values, or combinations thereof. In non-limiting embodiments, the dataset can be EWI images, EWU strain curves, or a combination thereof. In some embodiments, the dataset can be an external dataset and/or an internal dataset obtained through a transducer coupled to the disclosed processor. In some embodiments, additional features can be added to the dataset. For example, categorical features such as the apical view type where the strain curves are retrieved from (e.g., 4-chamber, 3.5-chamber, 2-chamber or 3-chamber view) can be included as well as the type of acquisition used (e.g., a field of view depth and pixel resolution).

In certain embodiments, the disclosed classifier can select ZC candidates based on the collected features. For example, the machine learning (ML) classifier can be a binary classifier. The ML classifier can vote for the best ZC candidate. For example, the ML classifier can select ZC location candidates with the highest probability for each pixel and assign it with a label (e.g., 1). The ML classifier can swipe through a set of probability thresholds to find the best cutoff value (e.g., highest precision given a condition set on the recall, also known as sensitivity or true positive rate). Then, the ML classifier can pick the best ZC candidate if its probability is higher than the cutoff threshold and assign it the label (e.g., 1). The probability thresholds can range from 0 to 1, less likely candidates to most likely. For example, candidates with probabilities lying above thresholds set to 0.7, 0.8 or 0.9 can be considered as satisfying cut off values and selected. These candidates can be considered to have a high enough probability, sufficient to be assigned a label 1, while the others can be discarded and assigned a label 0.

In certain embodiments, the machine learning classifier can be trained with a training dataset. In non-limiting embodiments, the training dataset can include hyperparameters. For example, the logistic regression model can include hyperparameters (e.g., elastic net, L1-ration, etc.), the SVM model can include hyperparameters (e.g., kernel types), and the Random Forest model can include hyperparameters (e.g., n estimators). The machine learning classifier can be fitted on the training set with a set of given hyperparameters and evaluated its performance. In some embodiments, the training dataset can include both training and validation samples for improving the accuracy and efficiency of the machine learning classifier. For example, once the machine learning classifier and a set of hyperparameters that can yield appropriate results on the validation set are determined, the classifier can be refitted with these settings on the dataset constituted of both the training and validation samples for improving the ML model. In non-limiting embodiments, the training dataset can be ground truth samples to automatically select ZCx. The ground truth samples are manually generated isochrones. Isochrones can be the electromechanical wave imaging activation maps. In certain embodiments, the processor can be configured to automatically select using a heuristic-based baseline. In non-limiting embodiments, the Heuristic-based baseline can be an approach relying on certain hard coded values and pre-set conditions. For example, the heuristic-based baseline can select the first positive to negative ZC immediately following the QRS complex onset of the obtained incremental axial strain curve and occurring within a pre-determined search window (e.g., 200 ms). In non-limiting embodiments, the heuristic-based baseline can select the first positive to negative ZC that satisfies the pre-determined empirical conditions. In non-limiting embodiments, the pre-determined empirical conditions to determine the correct ZC candidate can be defined based on conditions on the negative ZC peak amplitude and the steepness of the strain curve slope at the crossing. For example, the methods of determining the pre-determined empirical conditions can include selecting the first positive to negative ZC that satisfies (1) $\text{epsilon\_min} \geq 20\% * \min(\text{epsilon\_min for any i})$ with i being any point contained in the 2D mask and considered for the generation of the activation map and (2) $|\text{slope ZC}| \geq 20\% * \max(|\text{slope strain curve for that given i}|)$, where slopeZC is the slope of the strain curve at each ZC location, and epsilon_max and epsilon_min is same as the maximum positive and minimum negative strain values surrounding each ZC.

In certain embodiments, the system can be configured to perform electromechanical imaging. The disclosed system can further include a transducer that can be configured to perform electromechanical wave imaging. For example, EWI images of a subject can be acquired through the disclosed transducer, which can generate a high frame-rate ultrasound sequence (e.g., up to about 2 seconds, up to about 4 seconds, up to about 6 seconds, or up to about 8 seconds) including a single diverging wave (e.g., at about 250 Hz, at about 500 Hz, at about 1000 Hz, or at about 2000 Hz, or between about 205 Hz to about 2000 Hz) acquired in four standard echocardiographic apical views. In non-limiting embodiments, the transducer can be a 2.5 MHz phased-array transducer. In some embodiments, the sequences can have a duration of about 0.5-2.5 seconds, framerates of about 250 Hz-4000 Hz and the transducer frequencies can vary from about 2 to 4 MHz. The processor can perform the displacement estimation on the radiofrequency signals from each element of the ultrasound probe/transducer with 1D axial cross-correlation (e.g., 10 wavelength window, 90% overlap). The processor can further calculate the axial strains from the displacement estimation by a least-squares estimator. The processor can be operatively coupled to the transducer. For example, the processor and the transducer can be coupled directly (e.g., wire connection or installation into the transducer) or indirectly (e.g., wireless connection).

In certain embodiments, the disclosed processor can identify multiple ZC candidates. In the apical views, since the ultrasound beam can be aligned with the ventricular myocardial wall that is shortening during systole, this corresponds to a positive-to-negative flip or downward ZC of the incremental axial strain. As incremental strain curves sometimes exhibit more than one negative peak after the onset of the QRS complex or p-wave (e.g., for the ventricular or atrial isochrones, respectively), instead of one clear ZC, multiple ZC candidates can be identified.

In certain embodiments, the disclosed processor can be configured to generate an activation map/EWI isochrone. The disclosed processor can be configured to perform beam-forming on an image acquired by the transducer, estimate the displacement of the tissue based on the image, and generate an incremental strain curve based on the displacement. For example, the myocardium of interest can be first segmented on the B-mode image. For about 150 randomly chosen points in the segmented mask, t the timing of the first significant change after the QRS onset can be selected manually/automatically on the incremental axial strain curves for the ventricles, respectively p-wave onset for the atria. A Delaunay triangulation-based cubic interpolation can then be applied to the 2D scattered activation time ZC values in order to achieve a continuous isochrone pattern throughout the entire myocardium mask grid. The activation timings in milliseconds can be color-coded on a 2D map or isochrone (e.g., with red being early activation and blue late). Once the maps have been generated in the four views, a 3D-rendering algorithm can automatically detect the longitudinal left ventricular (LV) median axis on the four apical isochrones. The multi-2D views can then be co-registered around that axis, and linear interpolation of the activation times can be performed around the circumference. This leads to 3D-rendered activation maps. The machine learning classifier and/or heuristic-based baseline can reduce the time for generating the activation map/EWI isochrone, address the cases with multiple ZCs, and choose the best candidate consistently without observer bias. In non-limiting embodiments, the disclosed algorithm can perform the automated selection in less than about 30 seconds, about 20 seconds, about 10 seconds, about 5 seconds, about 3 seconds, about 1 seconds per isochrone. In some embodiments, if the algorithm is run with a given set of input parameters and strain curves, the disclosed algorithm can be configured to always give out the same results. Such algorithm can reduce the inter-observer variability, which can occur when more than two different human operators manually generate the isochrones (e.g., observer's bias).

In certain embodiments, the subject can include a Wolff-Parkinson-White patient, a healthy human, any animal models (e.g., canines), any patients after successful ablation procedures, an Atrial Flutter patient, a ventricular trachyacardia patient, or combinations thereof. In non-limiting embodiments, the disclosed model can be applied to any type of subjects and/or patients, as long as the training dataset can be updated in the meantime, and the model can be retrained to include such type of data.

In certain embodiments, the disclosed subject matter provides a method for electromechanical wave imaging (EWI) with automated activation map generation. An example method can include performing an automated selection of at least one zero-crossing location using a heuristic-based baseline and/or a machine learning classifier and generating an electromechanical wave imaging isochrone based on the automated selection.

In certain embodiments, through the heuristic-based baseline, the first positive to negative ZC immediately following the QRS complex onset of the obtained incremental axial strain curve and occurring within a pre-determined search window (e.g., 200 ms) can be selected. In non-limiting embodiments, through the heuristic-based baseline, the first positive to negative ZC that satisfies the pre-determined empirical conditions can be selected.

In certain embodiments, the automated ZC selection can be performed using a machine learning classifier. The machine learning classifier can be a logistic regression classifier, a support vector machine (SVM) classifier, or a Random Forest classifier. In some embodiments, the machine learning classifier can be a Random Forest classifier, which can include at least about 10, about 20, about 30, about 40, about 50, about 100, about 150, about 200, about 300, about 400, or about 500 estimators. In non-limiting embodiments, the machine learning classifier can be configured to have a precision rate of more than about 60%, about 70%, about 80%, about 89.5%, about 90%, or about 95%.

In certain embodiments, the method can further include collecting a plurality of features from a dataset. The features can include a spatial coordinate, a positive to negative zero-crossing time-point, a slope of a strain curve at each zero-crossing location, a maximum positive strain value surrounding each zero-crossing location, a minimum negative strain value surrounding each zero-crossing location, a time-point location of the maximum and the minimum strain values, or combinations thereof. In non-limiting embodiments, the disclosed classifier can select ZC candidates based on the collected features. For example, the ML classifier can vote for the best ZC candidate based on the collected features. The ML classifier can select ZC location candidates with the highest probability for each pixel and assign it with a label (e.g., 1). The ML classifier can swipe through a set of probability thresholds to find the best cutoff value (e.g., highest precision given a condition set on the recall, also known as sensitivity or true positive rate). Then, the ML classifier can pick the best ZC candidate if its probability is higher than the cutoff threshold and assign it the label (e.g., 1).

In certain embodiments, the dataset can be EWI images, EWU strain curves, or a combination thereof. In some embodiments, the dataset can be an external dataset and/or an internal dataset obtained through a transducer coupled to the disclosed processor. In some embodiments, additional features can be added to the dataset. For example, categorical features such as the apical view type where the strain curves are retrieved from (e.g., 4-chamber, 3.5-chamber, 2-chamber or 3-chamber view) can be included as well as the type of acquisition used (e.g., a field of view depth and pixel resolution).

In certain embodiments, the method can further include training the machine learning classifier with a training dataset. In non-limiting embodiments, the training dataset can include hyperparameters. For example, the machine learning classifier can be fitted on the training set with a set of given hyperparameters and evaluated its performance. In some embodiments, the training dataset can include both training and validation samples for improving the accuracy and efficiency of the machine learning classifier. In non-limiting embodiments, the training dataset can be ground truth samples to automatically select ZCx. The ground truth samples are manually generated isochrones. In some embodiments, the machine learning classifier can be trained to select at least one ZC by selecting a zero-crossing location with the highest probability for each pixel or selecting a zero-cross location that has a probability higher than a cutoff threshold. The cutoff threshold can be determined based on the sensitivity and/or true positive value of a dataset. By looking at precision and recall curves, a user can chose a satisfying cutoff threshold depending on its requirements for a given application. In non-limiting embodiments, a user can chose a threshold to favor high precision over high recall and vice versa. In some embodiments, the chosen cutoff value can be subjective and depends on the type of data on which the algorithm is being run.

In certain embodiments, the method can include receiving an external dataset and performing the automated selection using the external dataset. The external dataset can be EWI images, EWU strain curves, or a combination thereof. The external dataset can be obtained by other processors or experts.

In certain embodiments, the disclosed subject matter can provide improved imaging accuracy at a lower frame rate (e.g., between about 125 Hz and 500 Hz). For example, the disclosed device can be trained using the disclosed machine learning algorithm for electromechanical wave imaging. With the use of a Random Forest classifier for automated and semi-automated EWI estimation, thresholded on the prediction probability outcome and followed by a manual correction, the disclosed device can identify the status of the target tissue (e.g., early activated basal septum) or a subject in lower frame-rate cases while maintaining the electromechanical activation propagation pattern (e.g., over the rest of the myocardium). The lower framerate can range from about 125 Hz to about 500 Hz.

EXAMPLES

Example 1: Electromechanical Wave Imaging with Machine Learning for Automated Isochrone Generation EWI can be a viable assisting tool for non-invasive diagnosis, treatment planning and monitoring of ventricular and atrial arrhythmias in the clinic. However, standard isochrone generation can rely on manual selection of the ZC locations on the incremental axial strain curves for about 150 pixels in the segmented myocardium mask for each echocardiographic view and each patient. When considering large patient populations, this can become a time-consuming process.

Due to the plethora of images that can be acquired from patients in echocardiography (e.g., thousands per second), machine learning (ML) and deep learning can be used for ultrasound techniques, not only for i) image reconstruction and beamforming but also for ii) tumor detection and iii) segmentation of echocardiographic views with neural networks. The disclosed subject matter provides an improved EWI ZC selection processing pipeline. The disclosed subject matter can reduce inter-observer variability and possible bias of the manually generated isochrones while also decreasing the time needed to generate the activation maps towards real-time implementation. To achieve this goal, an automated zero-crossing detection algorithm relying either on heuristic-based baselines or machine learning classifiers was developed. The disclosed subject matter provides methods for training machine learning models to automatically generate isochrones. The disclosed subject matter also provides suitable supervised machine learning algorithms, which can result in a faster overall isochrone generation process while also preserving the accurate electromechanical activation pattern from manual generation.

Electromechanical Wave Imaging: EWI relies on a 2-second high frame-rate ultrasound sequence composed of a single diverging wave at 2000 Hz, acquired in four standard echocardiographic apical views on a Vantage 256 research scanner (Verasonics Inc., Kirkland, WA, USA) with a 2.5 MHz phased-array transducer (ATL P4-2, Philips, Andover, Massachusetts). The displacement estimation is performed on the radiofrequency signals from each element of the ultrasound probe with 1D axial cross-correlation (10 wavelength window, 90% overlap), followed by a least-squares estimator to derive the axial strains (5-mm kernel).

The wavefront of the electromechanical activation is defined as the time point at which the incremental strain value changes from relaxation to contraction. In the apical views, since the ultrasound beam is aligned with the ventricular myocardial wall that is shortening during systole, this corresponds to a positive-to-negative flip or downward ZC of the incremental axial strain. For most strain curves, a single negative peak exists during systole, and in these cases, the selection of the ZC location is straightforward. However, incremental strain curves sometimes exhibit more than one negative peak after the onset of the QRS complex or p-wave for the ventricular or atrial isochrones, respectively. In these instances, instead of one clear ZC, multiple ZC candidates are identified.

In the standard EWI isochrone generation process, the myocardium of interest is first segmented on the B-mode image. For about 150 randomly chosen points in the segmented mask, the operator manually selects on the incremental axial strain curves the timing of first sign change after the QRS onset for the ventricles, respectively p-wave onset for the atria. A Delaunay triangulation-based cubic interpolation is then applied to the 2D scattered activation time ZC values in order to achieve a continuous isochrone pattern throughout the entire myocardium mask grid. The activation timings in milliseconds are finally color-coded on a 2D map or isochrone, with red being early activation and blue late. Once the maps have been generated in the four views, a 3D-rendering algorithm automatically detects the longitudinal left ventricular (LV) median axis on the four apical isochrones. The multi-2D views are then co-registered around that axis, and linear interpolation of the activation times is performed around the circumference. This leads to 3D-rendered activation maps. The full standard manual EWI isochrone generation processing pipeline can take up to 90 minutes and runs in MATLAB.

To address the cases with multiple ZCs and choose the best candidate consistently without observer bias from the standard manual approach, the automated isochrone generation algorithm was developed.

Developing the automated algorithm: prior to feature detection and ZC selection on the incremental axial strain curves, a search window was set to 200 ms after the QRS origin picked on the single-lead ECG, outside of which ZC candidates are not assessed (vertical dotted line on FIG. 1). This assumption is based on the fact that the ventricles are expected to have fully activated within that 200 ms range. Healthy subjects with no history of ischemia, infarct or other co-morbidities were included. In the case of pathological cases, the search window can need to be extended to a longer time interval to make sure any ZC candidate are not missed in the abnormal myocardial tissue.

The disclosed subject matter can automatically collect the following features, as illustrated in FIG. 1:

1) (Xi, Yi): spatial coordinates of each point within the segmented myocardial mask, with $i \in [1: k]$; e.g., a limit of 150 pixels (k=150) can be applied when comparing the automated results directly to manually generated isochrones.

2) $tZC_{,1,n}$: all positive to negative ZC time-points (activation timings in ms), with n index of the ZC (e.g., n=1 if only single ZC possible or n=2 on FIG. 1).

3) $slope_{ZC}$: slope of the strain curve at each ZC location (dotted tangent line on FIG. 1).

0) $\in$ max and $\in$ min: maximum positive and minimum negative strain values surrounding each ZC.

4) $t_{\in max}$ and $t_{\in min}$: time-point locations of the maximum and minimum strain values (in ms).

The points with single ZC occurrences (n=1) are referred to as "stable ZCs," compared to "ZC candidates" when multiple options are available (n >1). In the 35 ground truth datasets included in this assessment (section II.D.), stable ZCs represented 40% of the cases, while ZC candidates were present ≈60% of the time.

Defining heuristic-based automated approaches as a reference baseline: once the incremental axial strain curve features were collected, two heuristic-based automated approaches were considered and compare the resulting isochrones for each one of them to the manually generated ground truth maps. The approaches were implemented as follows in MATLAB:

1) Naive approach: always select the first positive to negative ZC immediately following the QRS complex onset and occurring within the 200 ms search window.

2) Rule-based approach: select the first positive to negative ZC that satisfies the following empirical conditions:

$$\in_{min} \geq 20\% \; min(\in_{min} \forall i) \tag{1}$$

$$|slope_{ZC}| \geq 20\% \; max(|slope_{strain \; curve}|) \tag{2}$$

These ZCs, defined based on conditions on the negative ZC peak amplitude and the steepness of the strain curve slope at the crossing, were referred to as "clear" ZCs. The second approach tries to mimic the observer's reasoning when there is more than one ZC candidate to choose from. In fact, these two conditions (1) and (2) on the strain curve's slope at the location of the ZC and on the amplitude of the peak negative strain are common biases experienced by operators upon their manual ZC selection process.

Ground truth datasets: to be able to compare the performance of the different automated approaches, a method that can yield the most accurate physiological ZCs was developed, and the method was further confirmed whether the resulting isochrones preserve the accurate manually generated activation pattern or can outperform it. The algorithm was assessed with certain well-characterized datasets. Manually generated isochrones can be considered ground truth data if they have previously been validated by electroanatomical mapping (EAM).

First, twenty-four (N=24) Wolff-Parkinson-White (WPW) patients taken from the group's pediatric (14/24) and adult (10/24) clinical evaluations were assessed. The patients had ventricular pre-excitation but were known to be otherwise healthy with normal cardiac anatomy and function (e.g., no ischemia as it can have an effect on the strain curves due to tethering, for instance, or reduced strain amplitudes). Five (N=5) human cases were included in sinus rhythm from patients post successful WPW ablation.

In addition, data from prior open-chest canine cases with EAM validation on the epicardial surface of the LV using the clinical EnSite mapping system (Abbott Medical, St. Paul, MN, USA) was included. Contrary to patient data, this allowed us to achieve exact LV wall co-registration between the surface mapped and the wall portions being imaged in the apical views. This was accomplished after the thoracotomy by probing the epicardium with the mapping catheter, ensuring visualization on the corresponding B-mode before acquiring the views, and placing the associated labels on the electroanatomic maps. One canine was paced at a single antero-lateral LV location, while the other animal had 5 pacing electrodes positioned across its LV anterior surface, leading to a total of six (N=6) different LV-paced canine datasets.

TABLE 1

| Patient demographics in ground truth datasets. | | |
|---|---|---|
| Wolff-Parkinson-White patients (N = 24) | | |
| Gender | Male | n = 13 (54%) |
| | Female | n = 11 (46%) |
| Age (yrs) | Range | 7-67 |
| | Median | 17 |
| Patients in sinus rhythm (N = 5) | | |
| Gender | Male | n = 2 (40%) |
| | Female | n = 3 (60%) |
| Age (yrs) | Range | 7-17 |
| | Median | 12 |

Therefore, a total of 35 datasets with zero-crossings validated with the manual selection ground truths were assessed: 35 cases×4 apical views×150 spatial points=21000 incremental strain curves. These 21000 strain curves were all annotated by a single expert.

All datasets were previously acquired with a Vantage 256 research scanner. The human subject assessment was conducted under a protocol approved by the institutional review board (IRB) and was carried out in accordance with IRB guidelines and regulations. Informed consent was obtained from all participants. In parallel, the animal study protocol was approved by the Institutional Animal Care and Use Committee (IACUC) and was compliant with the Public Health Service Policy on Humane Care and Use of Laboratory Animals.

Machine learning classification models: a supervised learning model was subsequently built to classify the ZC candidates. Supervised learning consists of building a model that approximates a function trained with ground truth samples (i.e., labeled data). For each sample, this learned function takes features as an input and returns a value. A binary classifier for the disclosed subject matter needs to determine whether a ZC candidate is the correct one. In order to do so, the data was labeled: for a given pixel (Xi, Yi) in the segmented myocardium mask, the ZC candidate with the activation time $t_{ZCi,n}$ closest to the manually selected ZC location was assigned the label=1 (i.e., true location), while the others $t_{ZCi,n}$ with j≠n were assigned the label=0. The feature engineering process was performed on the above-mentioned ground truth datasets.

Pre-processing of the dataset was required prior to training the classification model. On top of the automatically collected numerical strain curve features listed above, the following categorical features were included: the apical view type the strain curves were retrieved from (4-chamber, 3.5-chamber, 2-chamber or 3-chamber view), as well as the type of acquisition used (i.e., a field of view depth and pixel resolution). The list of all features is provided in Table II with a total of 16 features=8 categorical features+8 numerical features.

TABLE 2

Features used for the machine learning algorithm.

| | Categorical features | Numerical features |
|---|---|---|
| 1 | Apical 4-chamber | $X_i$ coordinate |
| 2 | Apical 3.5-chamber | $Y_i$ coordinate |
| 3 | Apical 2-chamber | $t_{ZC_{i,n}}$ location |
| 4 | Apical 3-chamber | $slope_{ZC}$ slope at ZC location |
| 5 | 14-cm deep field of view | $\epsilon_{max}$ peak positive strain before ZC |
| 6 | 20-cm deep field of view | $\epsilon_{min}$ peak negative strain after ZC |
| 7 | $\lambda$/16 pixel axial resolution | $t_{\epsilon_{max}}$ peak location before ZC |
| 8 | $\lambda$/8 pixel axial resolution | $t_{\epsilon_{min}}$ peak location after ZC |

The "one-hot encoding" was performed on the categorical features, which includes converting categorical variables into a binary form that can be provided as a feature to train the ML algorithm. The last pre-processing was to standardize the numerical features in order to convert them to a common scale with an average of zero and a standard deviation of one. This was achieved with z-normalization: (Xi, Yi) standardization was performed by the patient and by view for consistent distance measurement purposes across cases, while the other numerical features were standardized across patients prior to training.

The developed machine learning algorithm can be a binary classifier. For each P (Xi, Yi) with no stable ZC, the algorithm has to vote for the best ZC candidate. Therefore, the disclosed system can learn a function f that can map the features described above to a probability $p \in [0:1]$ of being a true ZC, and predict that the candidate with the highest probability is indeed the ZC, while the others are not. To find the most appropriate algorithm, three classic machine learning approaches were evaluated: Logistic Regression, Support Vector Machine (SVM) and Random Forest. Logistic regression is a widely used statistical generalized linear model, often chosen as a reference baseline in ML, as it is simple and straightforward to implement. The logistic regression classifier used herein relied on an elastic net regularization, linearly combining L1 and L2 regularization techniques on the regression coefficients included in the penalty term of the loss function. The corresponding hyperparameter, in this case, is called the L1-ratio: being equal to 1 if the penalty term is only an L1 regularization, while equal to 0 if it's only an L2 regularization (Table III).

TABLE 3

Machine learning models associated hyperparameters and a list of corresponding values used upon interactive tuning.

| ML model | Hyperparameters | Values used for iterative tuning |
|---|---|---|
| Logistic regression | elastic net, L1-ratio | [0, 0.1, 0.2, 0.3, 0.4, 0.5, 0.6, 0.7, 0.8, 0.9, 1] |
| SVM | kernel type | 'linear', 'poly', 'rbf', 'sigmoid' |
| Random Forest | n estimators | [20, 50, 100, 200, 300, 400, 500] |

Poly = polynomial, rbf = radial basis function, n estimators = number of estimators of trees in the forest.

SVM, also known as support vector networks, is a supervised learning model used for classification, which defines a hyperplane to divide the two categories. The SVM kernel can define what type of separation can be applied between the classes and allows to find the optimal hyperplane in a different dimensional space. Random Forest is an ensemble learning method for classification that operates by constructing a multitude of decision trees. Random Forest can be good for dealing with heterogeneous features. Each decision tree gives a predicted label to the samples, and the Random Forest ends up assigning the label that has the most votes out of all the decision trees. All models were implemented in Python with the Scikit-learn library to define the three classifiers and their associated hyperparameters (Table III).

Furthermore, two voting options that can convert the probability values of the ZC candidates to binary labels and determine the predicted labels for each candidate were assessed the correct ZCs for each P (Xi, Yi):

1) Always select the highest probability ZC candidate for each pixel and assign it the label=1:

$$\arg\max_n \left( p\left(t_{ZC_{i,n}}\right) \right) \forall (X_i, Y_i) \tag{3}$$

2) Swipe through a set of probability thresholds to find the best cutoff value: highest precision given a condition set on the recall (also known as sensitivity or true positive rate). Then, pick the best ZC candidate only if its probability is higher than the cutoff threshold, and assign it the label=1:

$$\arg\max_n \left( p\left(t_{ZC_{i,n}}\right) \right) \text{ only if } p\left(t_{ZC_{i,n}}\right) > p_{thres} \tag{4}$$

These approaches were evaluated on the validated ground truth cases. The 24 WPW datasets were split into a training set and a validation set with a 70/30 ratio: 16 patients for training (9614 labeled strain curves) vs. 8 for evaluating the hyperparameters (4453 strain curves). The hyperparameter tuning process was iterative: a model was fitted on the training set with a set of given hyperparameters and was evaluated its performance on the validation set. The approach taken was that of a grid search, where it is iteratively swept through all possible combinations of hyperparameters for a given model within ranges (Table III). The performance of the different models was compared based on evaluation metrics described in more detail in the next paragraph, computed on the validation set. Once a machine learning algorithm and a set of hyperparameters that yielded good results on the validation set were identified, the model with these settings was refitted on the whole dataset constituted of both the training and validation samples. This method allowed for larger sample size in order to fit an improved model. The subsequent model was also evaluated on a held-out set called the test set. The latter included the remaining 11 ground truth datasets not used so far: 5 human sinus rhythm subjects and 6 LV paced canines. This test set was used only once to avoid leaking information to the hyperparameter tuning process and damaging the generalizability of the disclosed model by overfitting it to the test set. The resulting testing metrics can be the true performance evaluation of the disclosed model since they were obtained on a dataset that was neither used to fit the model nor used to select hyperparameters (Table 4, b-c). Performance was evaluated based on a) the validation dataset, b) the human test dataset, c) the canine test dataset. The three models displayed the performance for their tuned hyperparameters: L1-ratio=0.5, kernel=radial basis function, and n estimators=200.

15

TABLE 4

| Machine learning models performance evaluation. | | | | |
| --- | --- | --- | --- | --- |
| Highest probability ZC | | Probability threshold on ZCs | | |
| Precision | Recall | Precision | Recall | $P_{thres}$ |
| a) | | | | |
| 71.19% | 71.19% | 71.20% | 71.17% | 0.254 |
| | | 76.81% | 40.02% | 0.643 |
| 89.51% | 89.51% | 93.14% | 70.18% | 0.767 |
| | | 97.80% | 42.02% | 0.938 |
| 89.58% | 89.58% | 92.69% | 70.31% | 0.720 |
| | | 97.86% | 41.05% | 0.915 |
| b) | | | | |
| 57.16% | 57.16% | 57.16% | 57.16% | 0.200 |
| | | 57.16% | 57.16% | 0.200 |
| 88.41% | 88.41% | 93.07% | 70.12% | 0.775 |
| | | 96.61% | 40.18% | 0.937 |
| 89.53% | 89.53% | 92.74% | 70.06% | 0.721 |
| | | 97.52% | 40.09% | 0.903 |
| c) | | | | |
| 61.67% | 61.67% | 61.67% | 61.67% | 0.221 |
| | | 61.91% | 40.43% | 0.576 |
| 88.26% | 88.26% | 88.68% | 70.03% | 0.698 |
| | | 91.12% | 40.06% | 0.919 |
| 90.59% | 90.59% | 92.61% | 70.05% | 0.704 |
| | | 97.13% | 40.01% | 0.912 |

Row labels for each section a), b), c): Logistic regression, SVM, Random Forest (each spanning two data rows).

Although generalizability is a central issue in machine learning, the disclosed system was improved by different test datasets that illustrate various realistic tasks, such as a different set of patients or transferability of the model's predictivity to canine subjects.

Evaluation metrics: in order to evaluate the performance of the automated machine learning algorithms, the metrics used were the following:

$$\text{precision} = \frac{TP}{TP + FP} \text{ and recall} = \frac{TP}{TP + FN} \tag{5}$$

with TP=true positive, FP=false positive and FN=false negative. The precision can represent what portion of the prediction is true, while the recall corresponds to how many true ZCs were identified overall.

Figures 2A, 2B, 2C:
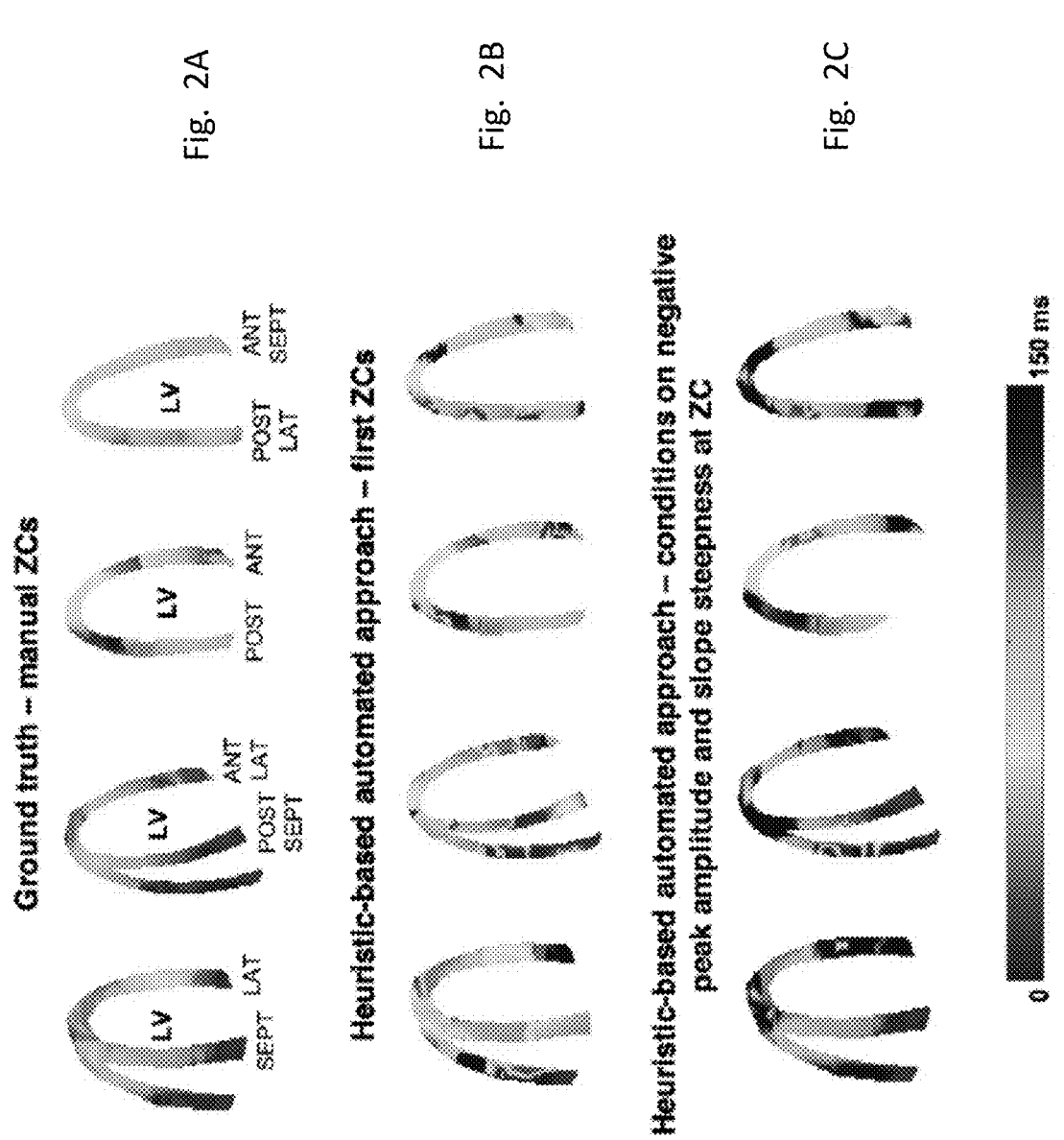
FIGS. 2A-2C provides diagrams showing multi-2D isochrones generated with different heuristic-based automated approaches for 2A) manual ground truth, 2B) naïve heuristic-based automated approach selecting the first occurring ZCs, and 2C) rule-based automated approach selecting the ZCs satisfying pre-determined conditions in accordance with the disclosed subject matter.

Multi-2D isochrones on an illustrative example corresponding to the canine testing dataset are shown in FIG. 2 for the ground truth manual zero-crossings, as well as for the two heuristic-based automated approaches. The anterior LV paced canine case satisfyingly exhibited a single early activated region on the ground truth manual isochrones, displayed in red on the LV anterior wall of the apical 2-chamber view (FIG. 2-a). While the first occurring ZCs approach did catch the pacing electrode's (earliest activated) region, it also displayed several other early activated areas, even on the right ventricular (RV) free wall very distal from the location of the pacing electrode (FIG. 2-b). Furthermore, the isochrones generated with the negative peak amplitude and slope conditions (1) and (2) were less noisy and more similar to the manual ground truth in terms of predominantly late activated blue color and overall activation pattern, despite missing the pacing electrode's location on the anterior wall of the apical two-chamber view (FIG. 2-c). None of the two heuristic-based automated approaches were very convincing.

Regarding the machine learning classification models, the set of tuned hyperparameters that was found to yield the best

Figure 3A:
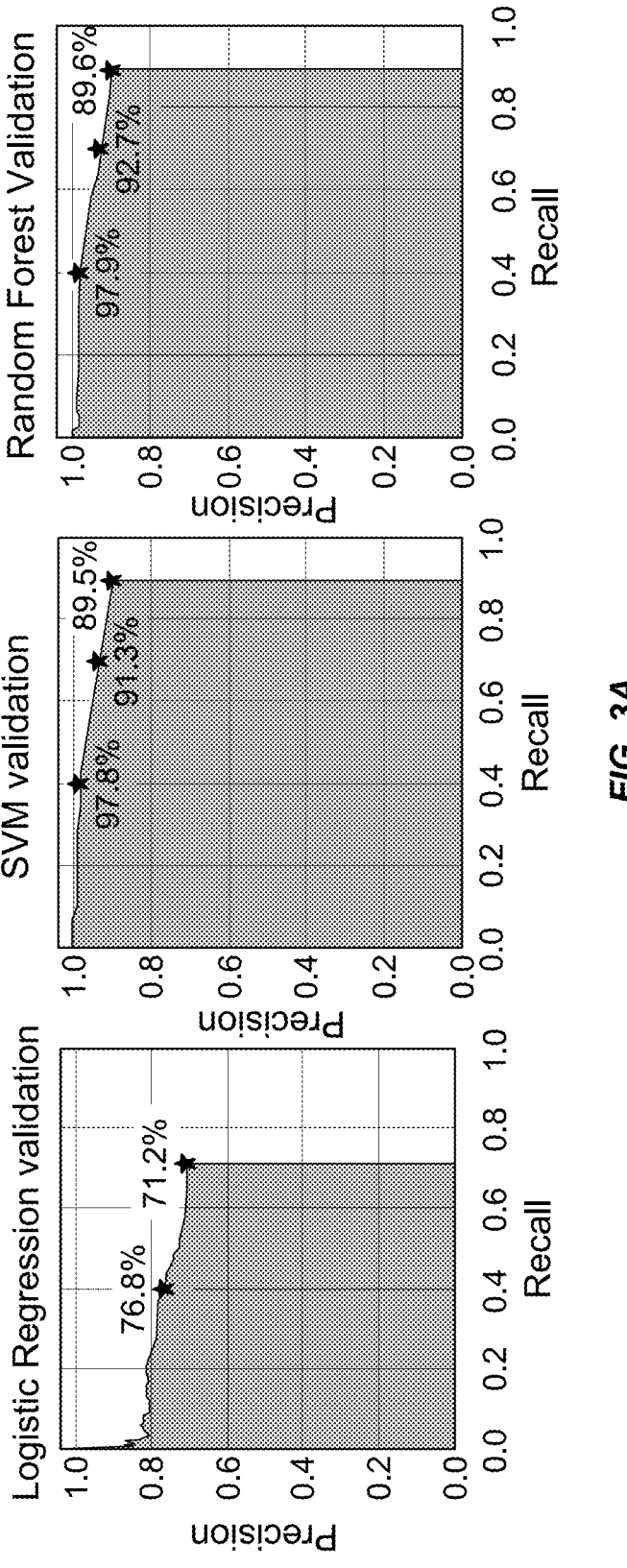
FIGS. 3A-3C provide graphs showing precision-recall curves for the three machine learning (ML) models (logistic regression, SVM, and Random forest) based on 3A) the human validation dataset, 3B) the human test dataset, and 3C) the canine test data set in accordance with the disclosed subject matter.
Figure 3B:
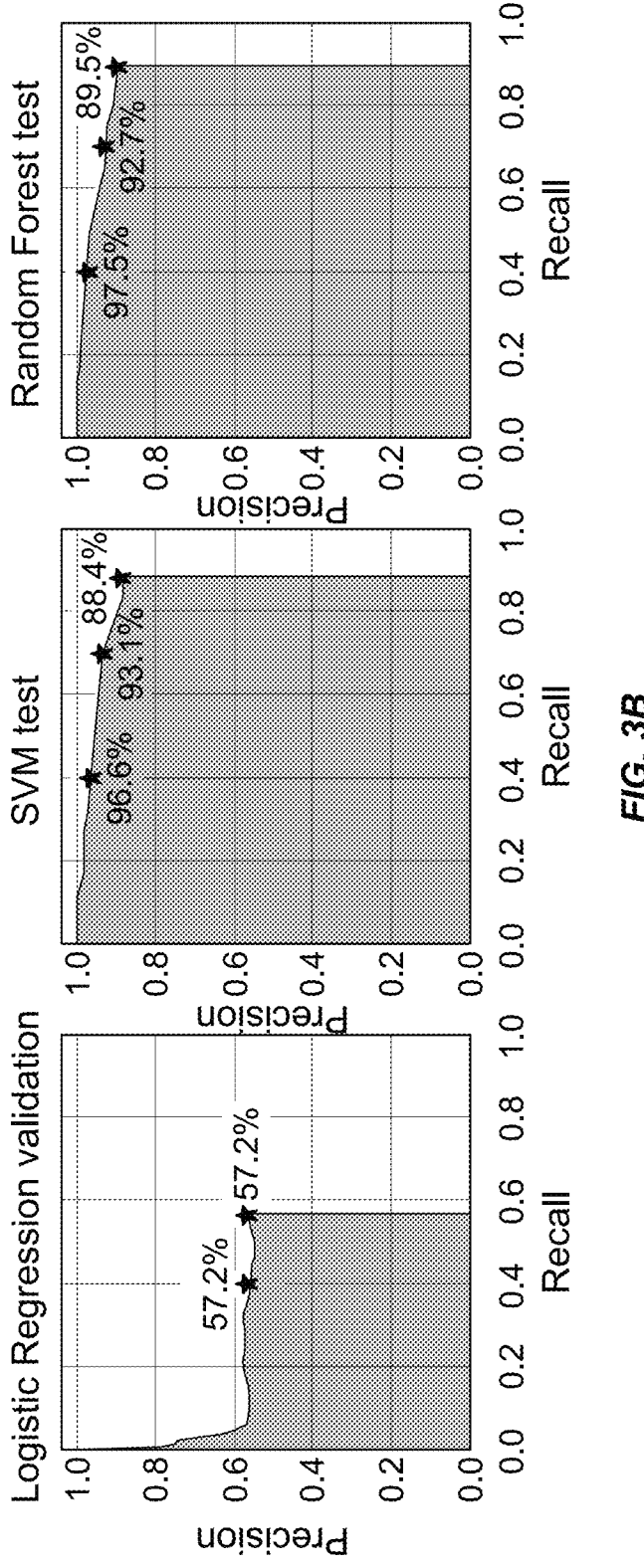
Figure 3C:
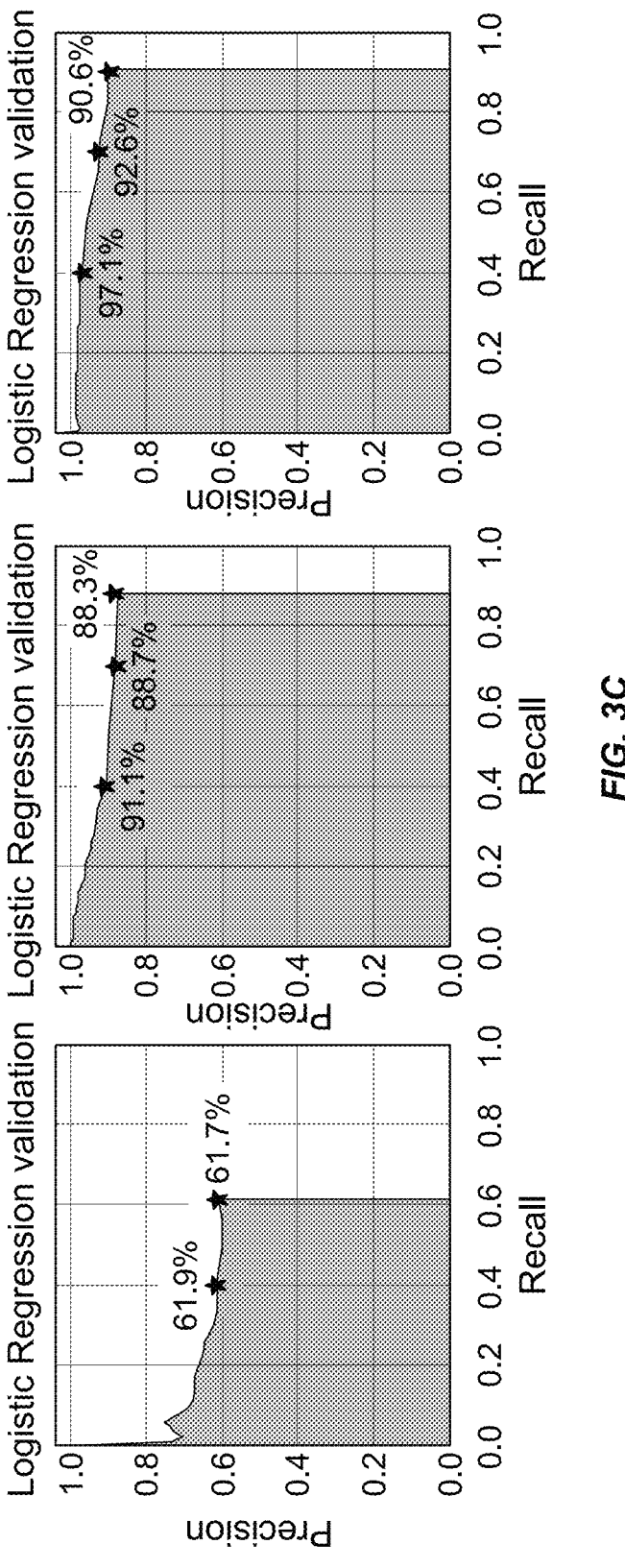
Figures 4A, 4B, 4C:
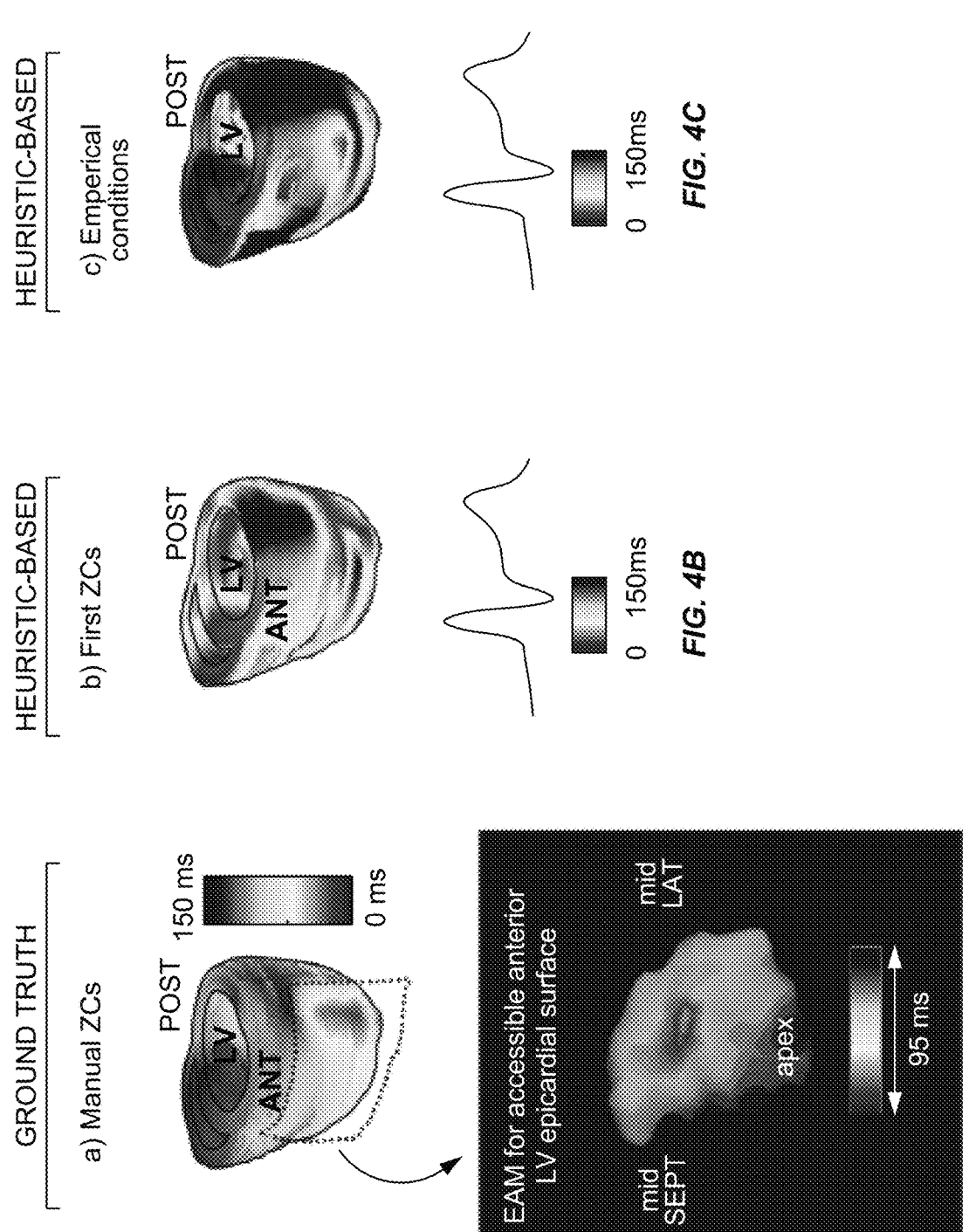
FIGS. 4A-4F provide diagrams showing 3D-rendered isochrones generated with 4A) manual ground truth, 4B) naïve heuristic-based automated selection (i.e., selecting the first occurring ZCs, 4C) another naïve heuristic-based automated selection (i.e., selecting ZCs satisfying predetermined conditions), 4D) logistic regression classifier, 4E) SVM classifier, and 4F) Random Forest classifier in accordance with the disclosed subject matter.
Figure 4F:
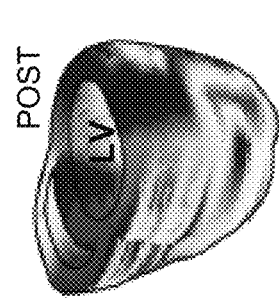
Figure 4F:
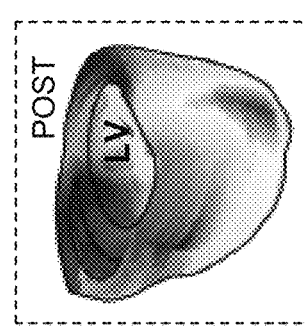
Figure 4F:
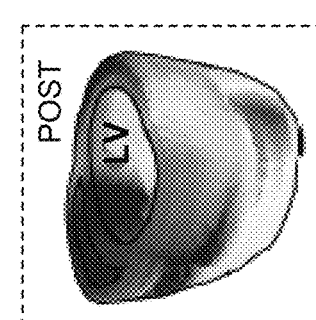
Figure 4E:
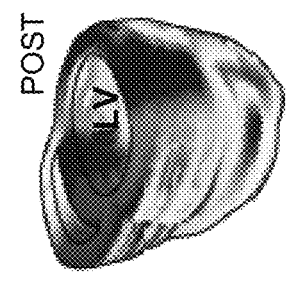
Figure 4E:
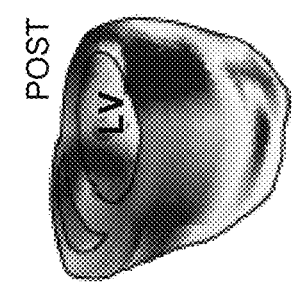
Figure 4E:
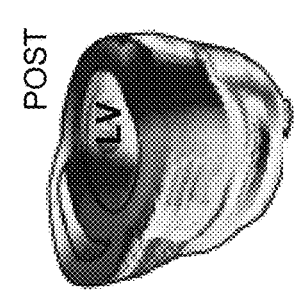
Figure 4D:
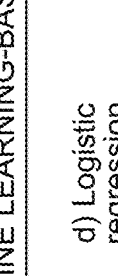
Figure 4D:
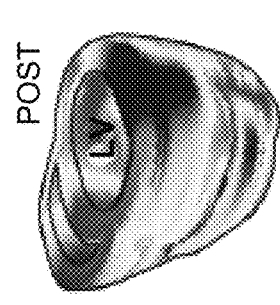
Figure 4D:
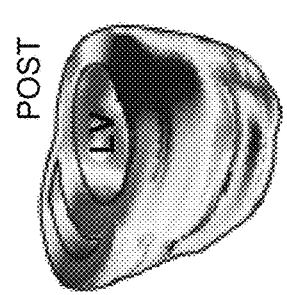

16 results (highest recall or sensitivity) on the validation set was the following: logistic regression, elastic net L1-ratio=0.5; SVM, kernel=radial basis function; and Random Forest, n estimators=200. The precision-recall curves for the three models (logistic regression in red, SVM in blue and Random Forest in green) were evaluated on the validation, human test and canine test datasets and are shown in FIG. 3. SVM and Random Forest are shown to significantly outperform logistic regression on all three datasets, while the two former performings similarly and not falling below 88% precision even in the worst case. Additionally, the stars and values overlaid onto the curves represent the performances for the different voting approaches and threshold scenarios used to generate the EWI isochrones throughout this paper, as explained in detail in Table 4. The recall value percentages (e.g., 70% and 40%) were selected based upon the assessment of the precision-recall curves for each machine learning model and each dataset. The two values were subsequently set as accepted thresholds that balanced between precision and recall rates and generated isochrones with the best quality tradeoff. Given that the assessment started with about 150 ground truth pixels P(Xi, Yi) for each apical view, a 70% recall can mean having at least 100 points with manually selected ZCs to choose from when generating the automated isochrones. However, setting a 40% recall (e.g., 60 pixels) can lead to spatial undersampling within the segmented myocardium mask and thus, drastically impact the isochrone activation pattern, which can then mostly result from interpolation and not actually selected activation times. Nevertheless, if the features were collected on about 2500 pixels per view, a larger pool of axial incremental strain curves can be used. In fact, once the models have been trained, the ground truth and labeled ZCs are not required on all the points to perform the testing on new data. Therefore, even with a low recall of 40%, the disclosed system still uses 1000 pixels, which corresponds to an order of magnitude higher than current standard manual EWI isochrone generation processes.

Quantitatively, Table 4 details the ML models' performance evaluated on the entire validation dataset (Table 4-a), as well as on both test datasets: human (Table 4-b) and canine (Table 4-c). The two different voting options for the multiple ZC candidates are shown: the highest probability approach always voting for a ZC candidate at all times, and the probability threshold option only voting for the best ZC candidate that satisfies the probability threshold condition. It is worth noting that the precision and recall values for the first voting approach are equal to one another. This is due to the fact that the highest probability models always make a ZC candidate selection for each pixel. In that case, because of that specific voting process FN=FP and thus, the evaluation metrics formulas written above end up being the same. On the other hand, for the second ZC voting approach, the table displays the best precision performance for two scenarios: i) when satisfying a recall >70%, and ii) when satisfying a recall >40%, respectively. Lastly, the corresponding probability thresholds are explicitly listed in the last column for each case. As expected with the precision-recall tradeoff, when the recall decreases from 70% to 40%, the precision improves by at least 2% and up to 5% for both SVM and Random Forest models depending on the dataset of interest. In addition, even though SVM initially performed very similarly to Random Forest in terms of precision on the validation dataset as well as on the human testing dataset, SVM's precision exhibited a 5% drop on the canine testing set (Table 4-c). Meanwhile, Random Forest remained stable and barely witnessed any change in precision when applying the model to canine data.

Figure 5A:
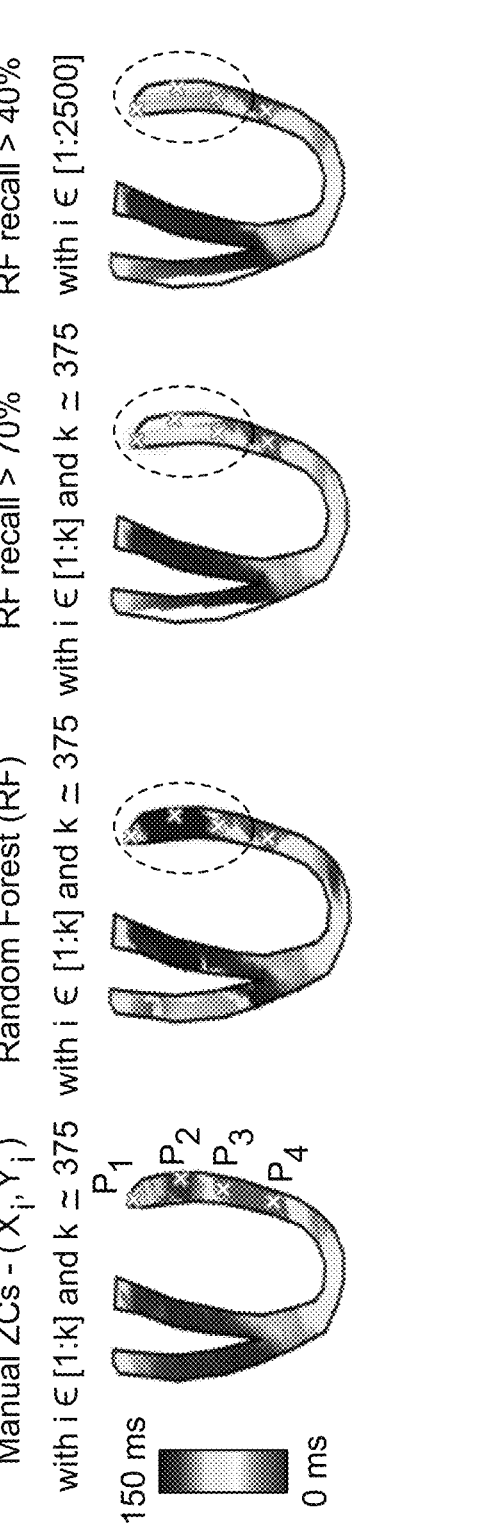
FIGS. 5A-5B provide 5A) myocardial isochrone mask indicating 4 points in the LV antero-lateral wall of the apical 3.5-chamber view from the LV paced canine and 5B) incremental axial strain curves for the 4 points with selected ZC candidates for each of the manual selection and three Random Forest approaches (e.g., no voting threshold, recall >70% and recall >40%) in accordance with the disclosed subject matter.
Figure 5B:
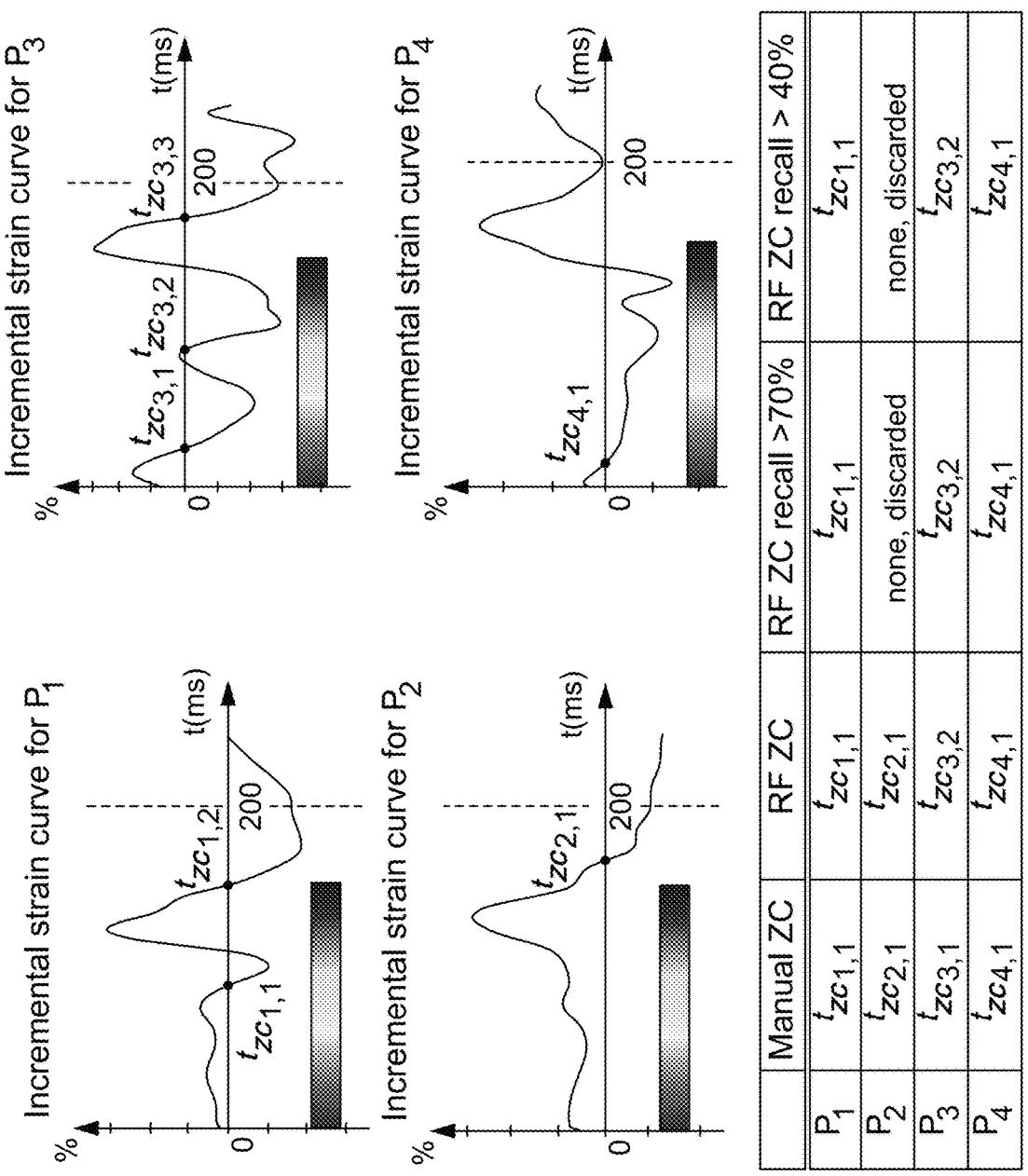

FIG. 4 illustrates the 3D-rendered isochrone results for the heuristic-based, and ML-based automated approaches on the example of an antero-lateral LV paced canine retrieved from the test dataset. The isochrone patterns of the heuristic naive baseline selecting the first ZCs and logistic regression automated approaches look very similar to one another (FIG. 4-b, d), but are far from comparable to the manual ground truth result (FIG. 4-a). Besides, the isochrone resulting from the rule-based heuristic approach does have a later blue activation pattern overall closer to the ground truth, despite missing the early activated region of interest from the LV pacing electrode in the antero-lateral region (FIG. 4-c). Meanwhile, SVM and Random Forest (FIG. 4-e, f, top row) outperformed the three other approaches and had promising qualitative performance, despite revealing discontinuities in the activation pattern anteriorly compared to the manually generated isochrone. The recall here was maximal since the models did not discard any pixel upon voting for the ZC candidates. In order to further increase the precision, the second voting option was used for applying a probability threshold to the ZC candidates and making sure the recall remained >70% (FIG. 4, middle row). In that case, the best performing algorithm was the Random Forest model. The latter is emphasized here by the dashed box. This was indeed previously quantified and confirmed by the higher performance evaluation metrics (Table 4). Furthermore, when setting the voting condition such the recall was higher than 40%, while simultaneously considering a larger amount of pixels ($P(X_i, Y_i)$ with i∈[1:2500]) not previously used in the initial ground truth manual ZC selection (FIGS. 4E and 4F, bottom row), the Random Forest precision increased even more. In fact, the antero-lateral LV pacing spot displayed in red became more localized in the longitudinal direction and did not spread towards the base anymore. Thus, the overall optimal automated algorithm that allowed the most successful localization of the antero-lateral LV pacing spot, as validated by the manual isochrones, is outlined by the green dashed box (Random Forest, recall >40% and 2500 pixels per view). Nevertheless, minor differences in the activation pattern remain visible at the basal level compared to the manual ground truth isochrone. These discrepancies are caused by the ZC selection process on the apical 3.5-chamber view for the Random Forest classifier when a probability threshold is applied to the ZC candidates upon voting and further emphasized by the subsequent interpolation of the activation times in 2D. Representative strain curves are displayed in FIG. 5B for four points located in the antero-lateral LV wall of the 3.5-chamber isochrone mask (FIG. 5A). The Random Forest voting approach with the recall conditions (both >70% and >40%) discarded some ZC points of lower confidence. This led to a reduced spatial sampling in that particular wall region, which resulted here, namely in P2 falling outside of the interpolated isochrone mask at the base and, therefore, explains the minor divergence from the manual isochrone (FIG. 5B).

Figures 6A, 6B, 6C, 6D:
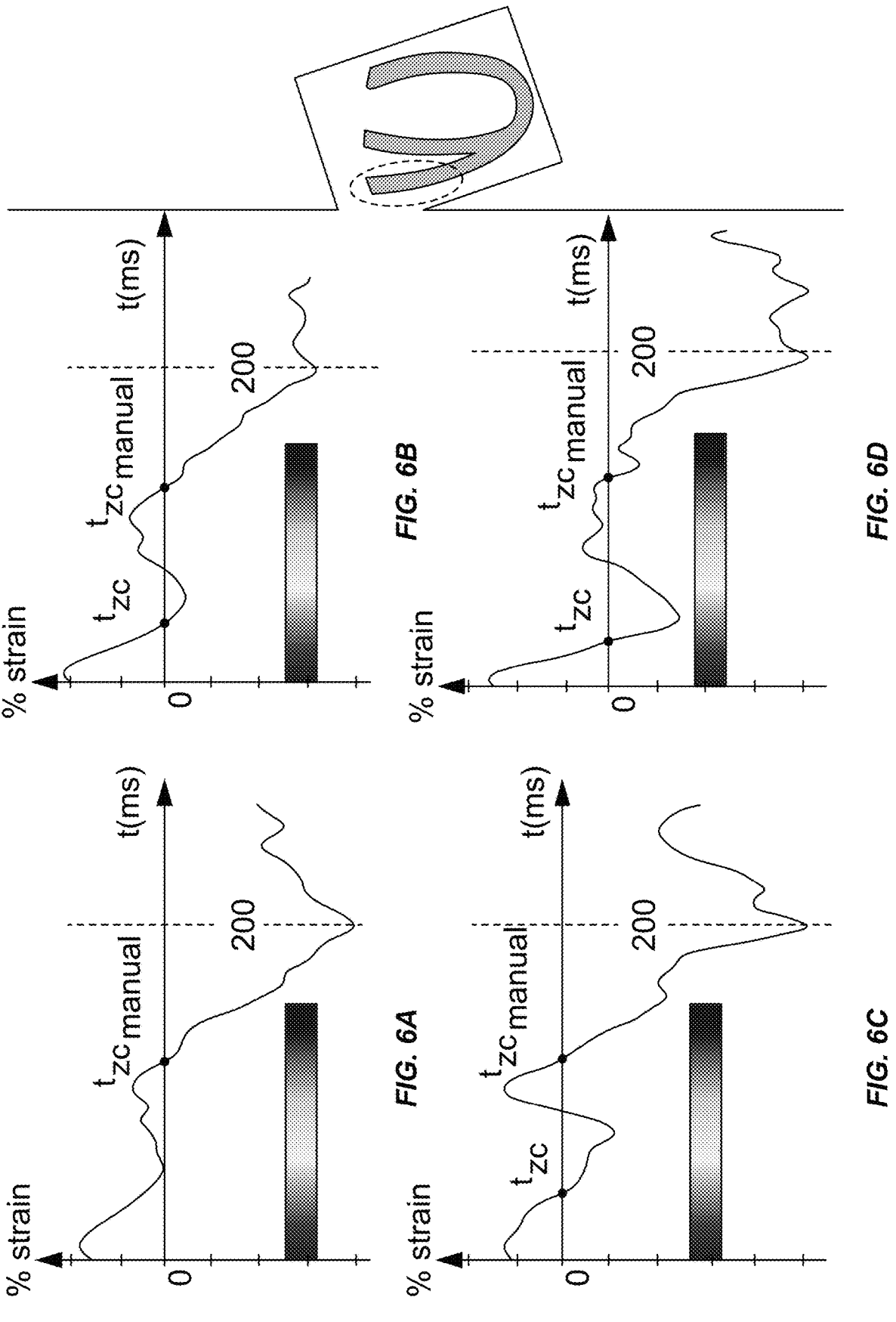
FIGS. 6A-6D provide diagrams and graphs showing incremental axial strain curves for 4 points in the RV free wall (black dashed outline) from the apical 3.5-chamber view isochrone of the antero-lateral LV paced canine 6A) with one ZC candidate (tzc manual) and 6B-6D) with at least two ZC candidates (tzc and tzc manual) in accordance with the disclosed subject matter.
Figure 8A:
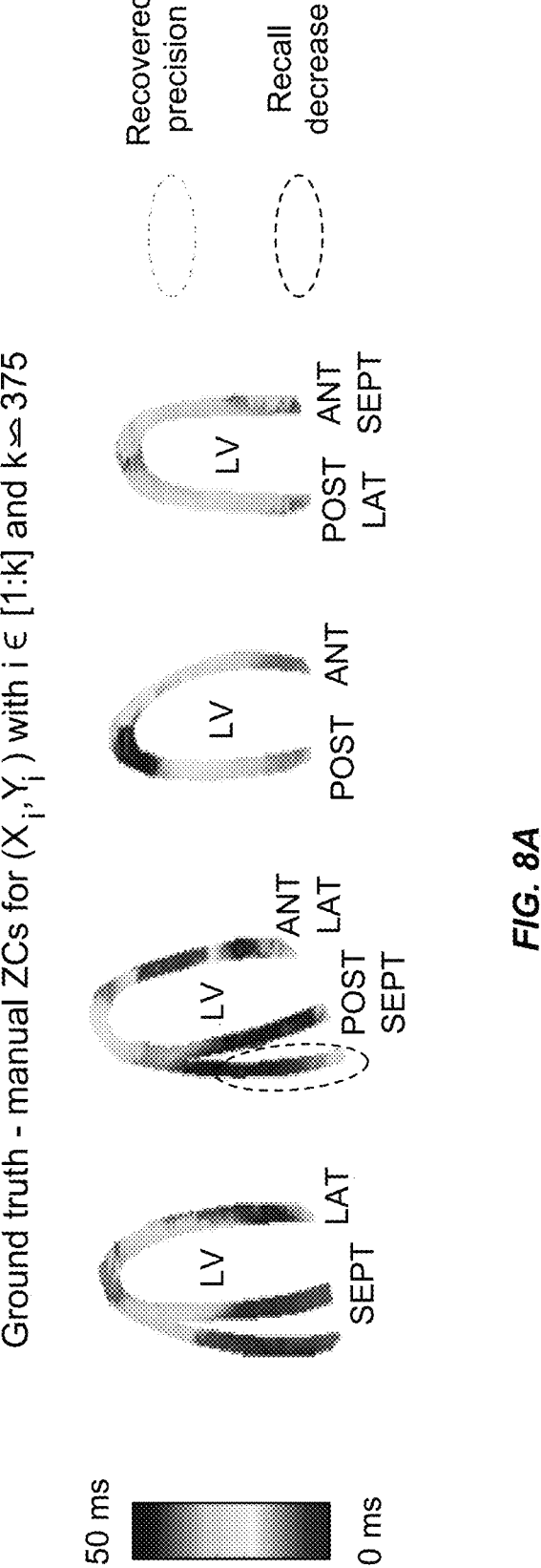
FIGS. 8A-8C provides diagrams showing multi-2D isochrones generated with 8A) ground truth (manual ZC selections), 8B) SVM classifier-based automated approach, and 8C) Random Forest classifier-based automated approaches on the example of the LV paced canine in accordance with the disclosed subject matter.
Figure 8B:
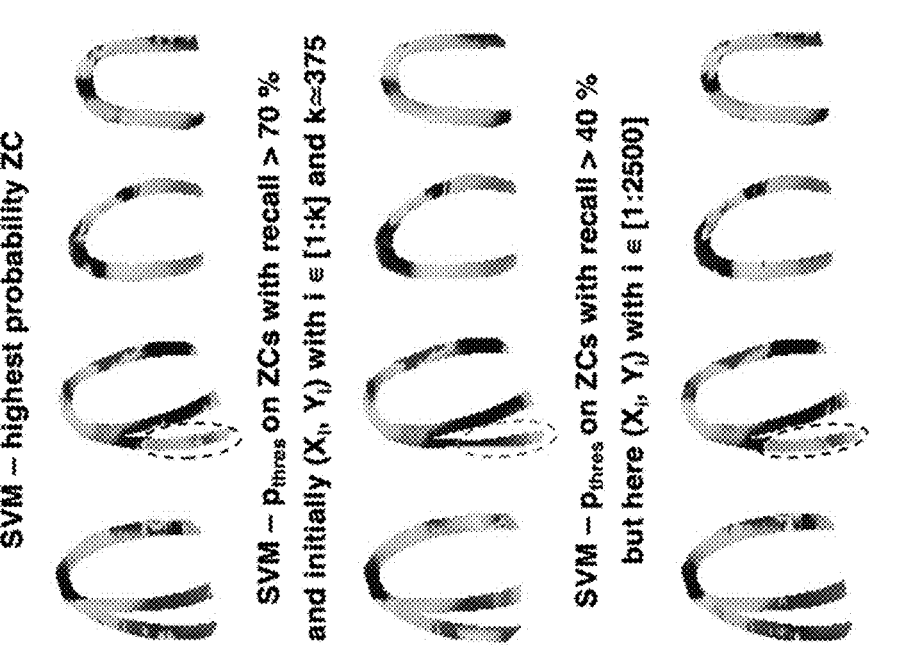
Figure 8C:
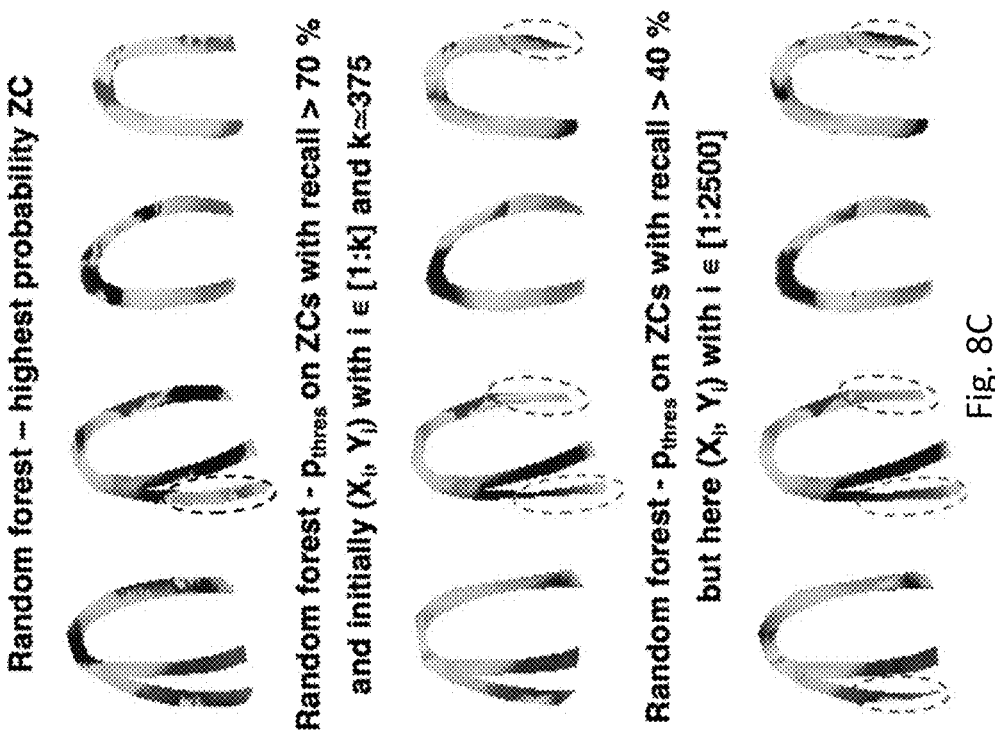
Figure 9A:
FIGS. 9A-9C provides diagrams showing multi-2D myocardial segmented masks used for 9A) ground truth based zero-crossing selection approach, 9B) SVM classifier based zero-crossing selection approach, and 9C) Random Forest based zero-crossing selection approach in accordance with the disclosed subject matter.
Figure 9B:
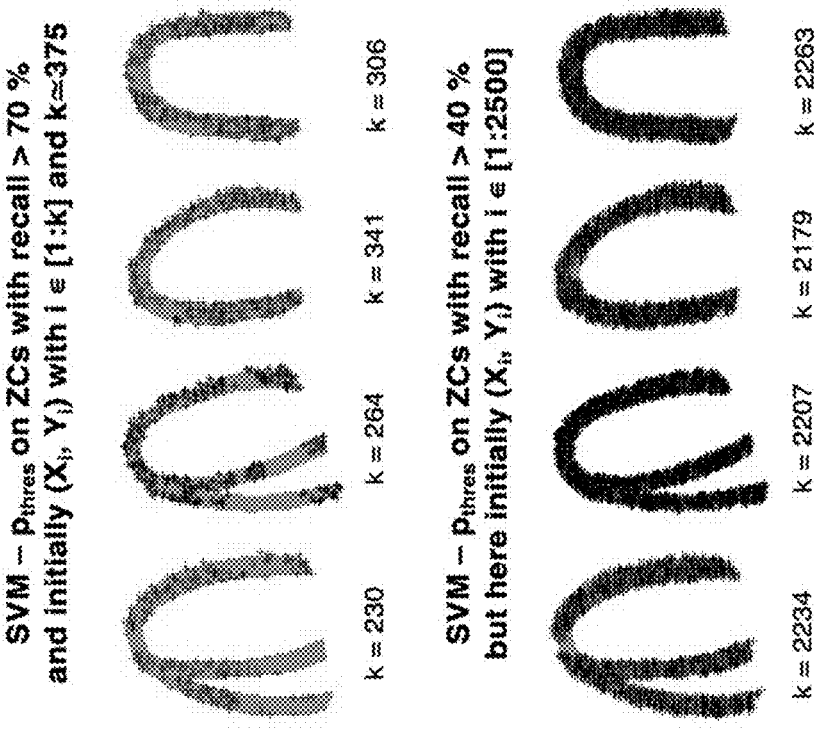
Figure 9C:
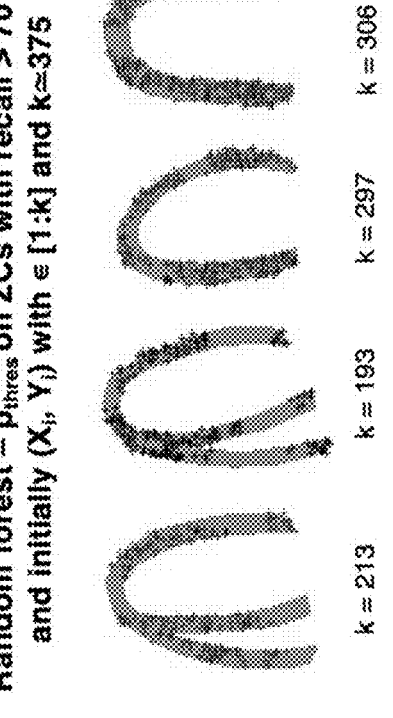
Figure 9C:
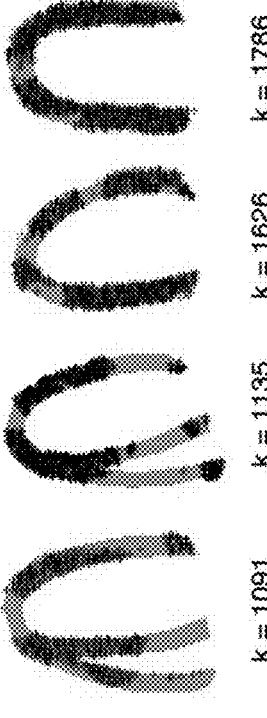
Figures 10A, 10B, 10C, 10D, 10E, 10F:
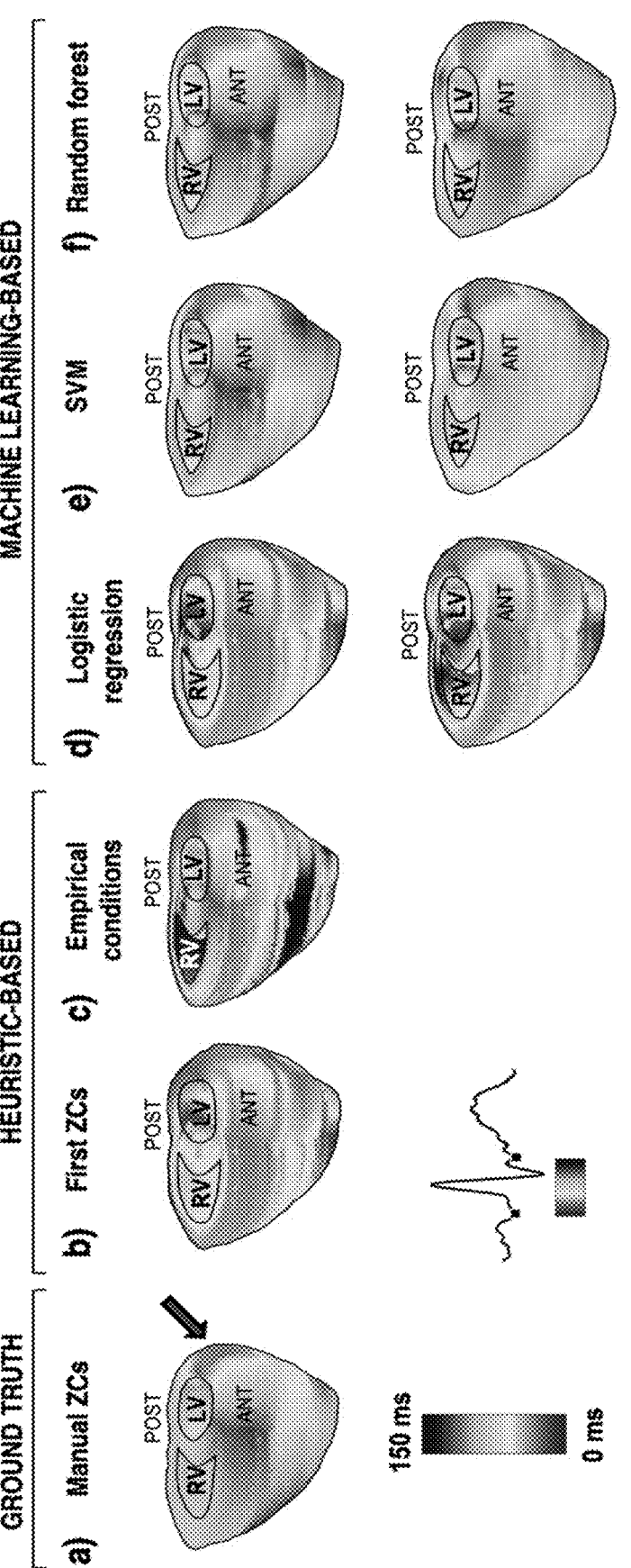
FIGS. 10A-10F provide diagrams showing 3D-rendered isochrones generated with different automated approaches on the example of a left lateral accessory pathway in a WPW patient taken from the validation dataset compared to the manually generated isochrone: 10A) Manual ground truth, 10B) Heuristic-based automated baseline selecting the first occurring ZCs, 10C) ML model with logistic regression classifier, 10D) ML model with logistic regression classifier 10E) ML model with SVM classifier, and 10F) ML model with Random Forest classifier in accordance with the disclosed subject matter.

Moreover, the comprehensive overview of the corresponding multi-2D EWI isochrone slices in all four apical views prior to 3D-rendering for the SVM and Random Forest models are included in FIGS. 8B and 8C, as well as the original ground truth manual 2D isochrones for that same LV paced canine (FIG. 8A). The 2D isochrones clearly demonstrate the improvements resulting from the second voting approach with the probability threshold, as well as the progress made when the model was applied to a larger number of pixels. The dashed circle outline where the precision was recovered when the recall decreased. FIG. 8 shows multi-2D isochrones generated with the two best ML-based automated approaches on the example of the LV paced canine (FIG. 4, FIG. 5 and FIG. 6) taken from the testing dataset compared to the manually generated isochrones. The EWI isochrones are shown for the manual ground truth, the SVM classifier and the Random Forest model. The two bottom rows correspond to the models results with the 2nd voting approach: probability threshold applied to the ZC candidates while satisfying a given set recall value. One difference for the very last row is the considerably larger amount of pixels the models were applied on, not previously used in the initial ground truth manual ZC selection. All ML algorithms generated the isochrones with their tuned hyper-parameters: elastic net L1-ratio=0.5; kernel=radial basis function and n estimators=2.

FIG. 6 and FIG. 9 further clarify the precision-recall tradeoff on this particular canine example. The pixel density is mapped spatially in each of the four apical views for all ZC voting scenarios (FIG. 9). FIGS. 9A-9C shows multi-2D myocardial segmented masks illustrating the (Xi, Yi) pixel locations (indicated by the black+) used for each zero-crossing selection approach on the previous antero-lateral LV paced canine example (FIG. 4, FIG. 5, FIG. 6, and FIG. 8). This illustrates how the Random Forest classifier can have lower confidence in particular myocardial wall regions but without risk voting for a ZC candidate in these regions, and can rather keep the precision metric higher than SVM by discarding more lower probability points, as previously shown and explained with P2 in FIG. 5. More specifically, FIG. 6 displays representative examples of incremental strain curves for 4 points in the segmented myocardium mask within the RV free wall of the 3.5-chamber view this time. The presence of a second earlier ZC candidate on three out of the four curves, different from the manually selected ground truth ZC, informs the change in the Random Forest model's behavior between the voting approaches in the recovered precision region with the recall conditions (green dashed circle).

Other examples of automated isochrones compared to manual ground truth are given in FIG. 7 and FIGS. 10A-10F, this time on a patient in sinus rhythm taken from the human testing dataset and a left lateral WPW case taken from the validation dataset, respectively. Once more, the Random Forest algorithm performed the best, clearly depicting the normal early activation of the atrioventricular node at the basal septum and the location of the accessory pathway on the left lateral wall of the LV. FIGS. 10A-10F show 3D-rendered isochrones generated with the different automated approaches on the example of a left lateral accessory pathway in a WPW patient taken from the validation dataset compared to the manually generated isochrone. The 3D-rendered EWI isochrones are shown for: a) Manual ground truth; b) Heuristic-based automated baseline selecting always the first occurring ZCs; c) ML model with logistic regression classifier; d) ML model with SVM classifier; and e) ML model with Random Forest classifier. The bottom row for (c-e) corresponds to the ML models results with the 2nd voting approach: probability threshold applied to the ZC candidates while satisfying a recall >70%. The ML model-based automated algorithms generated the isochrones (c-e) with their tuned hyperparameters: elastic net L1-ratio=0.5; kernel=radial basis function and n estimators=200.

In this optimization process, an automated zero-crossing detection algorithm was developed to generate EWI isochrones in a faster and more robust way, with no inter-observer variability. The disclosed system can use machine learning models for automatically selecting the best ZC candidates on axial incremental strain curves in WPW patients, sinus rhythm humans, and LV paced canines. The three ML models (logistic regression, SVM and Random Forest) were trained with manually selected zero-crossing features from past validated cases, therefore, considered as ground truth.

First, the models performance was evaluated with preci-sion-recall curves on the validation and testing datasets (FIG. 3). Both SVM and Random Forest models clearly outperformed logistic regression on all three datasets. In fact, the precision of the logistic regression classifier col-lapsed very quickly below 65% on the testing datasets, as illustrated on the middle and bottom rows precision-recall curves in red. Table 4 further describes the models' perfor-mance for the different voting approaches and probability threshold scenarios used to generate the EWI isochrones. The logistic regression model was not yielding a respective recall higher than 57.2% and 61.7% in the human and canine test datasets, despite applying the probability threshold to the ZC candidates with the voting approach. This led once more to situations where the precision was equal to the recall due to the maximum recall cutoff.

Additionally, even though SVM initially performed as well as Random Forests in terms of precision on the vali-dation and human testing datasets, it ended up not being as generalizable nor transferable to other types of datasets, like in the canine example for which it exhibited a 5% drop in precision (Table 4). The SVM model was more overfitted to the training and validation of human datasets. Meanwhile, Random Forest showed robustness, and its predictivity was not impacted by the type of dataset. This allowed building confidence about the future performance of the Random Forest model with respect to dealing with potential data it has not yet been exposed to. Thus, the Random Forest model with 200 estimators or trees was hereby proven to have the best performances overall no matter the dataset it was applied to. Setting a probability threshold upon ZC candi-date voting improved the precision from 89.5% to 92.7% and went as high as 97.5% on the testing datasets at the expense of a significantly lower recall (40%).

Figures 7D, 7E, 7F:
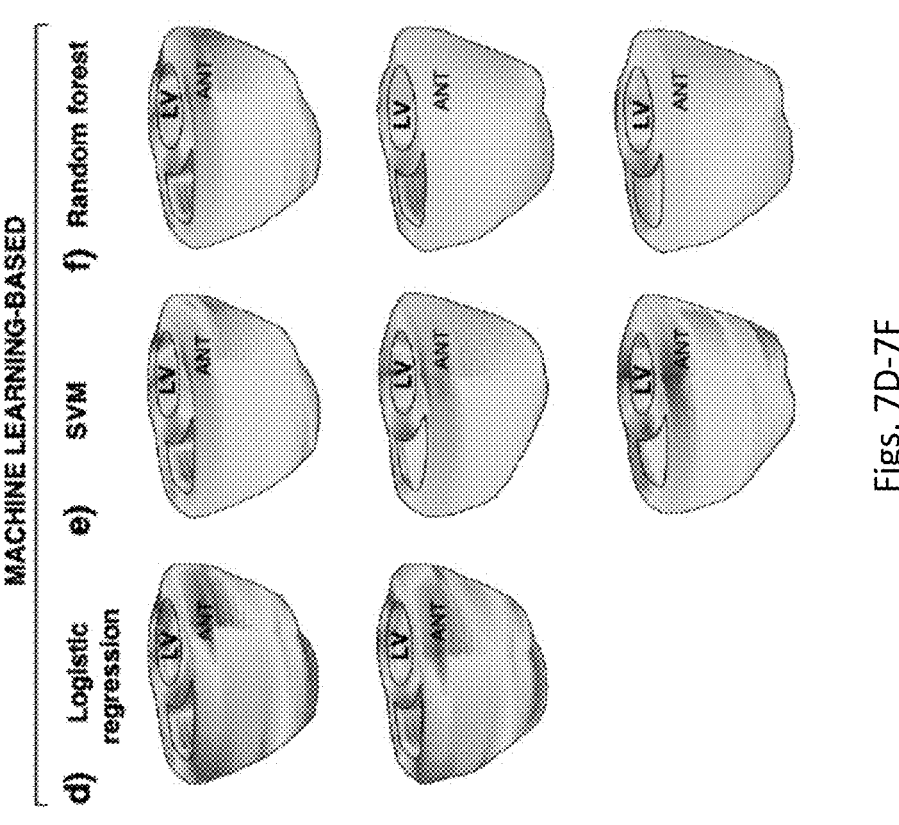

Furthermore, automated operator-independent 3D-ren-dered isochrone generation approaches such as SVM and Random Forest were shown capable of successfully identi-fying the accessory pathway in WPW patients, the normal early activated basal septum close to the atrioventricular node in sinus rhythm patients and the pacing electrode location in LV paced canines (FIG. 4, FIG. 5, and FIG. 7). The total processing time needed to generate the resulting 3D-rendered EWI activation maps decreased from the usual 90 minutes for the standard manual approach to less than 5 minutes per patient with the machine learning-based auto-mated approaches. More particularly, the times required for the ZC selection itself are listed in Table 5 for the three classifiers on the entire human and canine test datasets.

TABLE 5

| The processing time required for zero-crossing selection. | | |
|---|---|---|
| ML model | Human test dataset | Canine test dataset |
| Logistic regression | 1.6 seconds | 1.9 seconds |
| SVM | 43.9 seconds | 43.2 seconds |
| Random Forest | 40.9 seconds | 94.5 seconds |

The Random Forest can be deemed to have the best performance visually with the second voting approach while setting the condition on the recall evaluation metric (FIG. 4-$f$ and FIG. 7-$f$), outperforming SVM with the same probability threshold voting approach (FIG. 4-$e$ and FIG. 7-$e$). These findings were all the more true when considering a larger amount of pixels (2500 points) per apical view, not used in the initial ground truth manual ZC selection. Even if the incremental axial strain curves and associated features were no longer labeled, as they were not previously manually annotated, this allowed going as low as 40% for the recall value. In fact, the highest possible precision, no matter the recall, was identified. The resulting EWI isochrone activa-tion patterns were very satisfying. Despite discarding about 60% of the pixels per view and only making ZC predictions on 1000 points out of the 2500 (still more than four times the amount of pixels currently used for the standard manually generated isochrones), the precision rose above 97%.

Since the electromechanical activation constitutes a wavefront, it is expected to propagate continuously. There-fore, wen having several ZC candidates to choose from, that the correct and physiological approach can be to select the ZC that gives the smoothest transition in the activation gradient in order to decrease the amount of sudden "jumps" or discontinuities in activation times. The incremental strain curves, multi-2D isochrones and corresponding pixel loca-tions in the segmented masks, shown in FIGS. 6, 8 and 9, respectively, highlight that particular interesting behavior the Random Forest model adopted when faced with such a scenario. Three out of the four curves displayed the presence of a second earlier ZC candidate, different from the manu-ally selected ground truth ZC (FIGS. 6A-6D). An operator manually generating this 3.5-chamber view isochrone can most probably have applied a "nearest neighbor" approach: inferring which ZC candidate was the correct physiological one by looking at the nearest single stable ZC and choosing accordingly between the multiple candidates in the neigh-boring points. It seems the Random Forest classifier intrin-sically applied similar reasoning. This can also be justified by the highest amplitude of the second ZC negative peak strain. In fact, applying a condition on the negative peak amplitude can be a common bias experienced by the opera-tor upon his manual ZC selection process. Thus, it is possible that the training datasets included information regarding one zero-crossing candidate disappearing while another one appears with higher negative peak strain ampli-tudes, and the ML model can be predisposed to identifying such relationships because they were embedded in the training features. Investigating and further characterizing the effect of single versus multi-expert ground truth annotation on training bias is a topic of ongoing.

The disclosed subject matter provides automated EWI isochrone generation techniques with machine learning for the first time and an initial evaluation/optimization of the best classifier for zero-crossing selection. The Random Forest classifier can be further improved and increase its reproducibility by adding more categorical features (e.g., type of cardiac rhythm) as inputs to the ML model to potentially improve its robustness and transferability even more. Considering the totality of the points contained in the segmented myocardium mask in each view: (Xi, Yi) with i∈[1:k] and k >40000, instead of a subset of pixels with k≤2500, can also improve the isochrone outcomes at low recall values and decrease the suboptimal portion of the results.

The disclosed system can use a different learning approach, e.g., semi-supervised learning to increase the number of labeled samples included in the training dataset. In addition, the disclosed system can use a deep learning approach with no manual feature engineering, where the model can extract the features on its own. This can be achieved by directly feeding the incremental strain curve signals to a convolutional neural network (CNN) as the input data. Convolutional layers can extract useful knowledge and learn the internal representation of time-series data. In CNNs, different features can be extracted through convolution using filters whose weights are automatically learned during training. The disclosed automated isochrone generation process can include a regression task, in which the CNNs can need to find the correct ZC positions on the temporal strain curves and not classify the strain curves themselves. For real-time implementation of EWI, a combination of the automated system followed by manually adjusted ZC selection for isochrone generation can be used. An observer's input can help the ML classifier by manually labeling a limited number of samples for which the algorithm has the least confidence (e.g., some of the discarded pixels with lower ZC voting probabilities when the recall condition was set to 40%). Through "active learning," the model's learning process can be improved.

Electromechanical Wave Imaging with machine learning is disclosed herein to automatically detect zero-crossing time points on incremental axial strain curves for a faster, more robust, and less operator-dependent isochrone generation process. The Random Forest classifier showed improved results compared to logistic regression and SVM: capable of identifying accessory pathways as well as pacing locations in humans and canines, respectively, while also resulting in the most precise isochrone activation patterns. Against these findings, the standard manual processing pipeline required to obtain EWI activation maps can be abbreviated without a significant tradeoff in accuracy.

Example 2: Automated Electromechanical Wave Imaging at Reduced Frame Rates During Sinus Rhythm Using Machine Learning Spatial resolution can be prioritized over temporal in certain echocardiography, which restricts the use of time-shifted-based techniques at higher frame rates (FR). Electromechanical Wave Imaging (EWI) is an echocardiography-based modality that non-invasively maps the cardiac activation sequence at a high frame rate. At lower FRs, EWI strain curves have a different profile which constrains manual input and interpretation. The disclosed machine learning (ML) can assist in the accurate activation time estimation at low FR data. The disclosed subject matter can use a Random Forest classifier for automated and semi-automated EWI estimation, set thresholds on the prediction probability outcome followed by manual correction. The disclosed subject matter successfully identified the normal, early activated basal septum in normal sinus rhythm lower FR cases (N=6 FRs of 500 Hz, 250 Hz, 125 Hz) while maintaining the electromechanical activation propagation pattern over the rest of the myocardium. These findings indicate that ML can be used to generate accurate EWI activation maps with a more flexible FR range that includes clinical systems at low FRs, where manual processing would otherwise be impractical and/or inaccurate.

The cardiac disease remains the leading cause of death worldwide, with one out of three deaths attributed to heart disease each year. An early and accurate diagnosis of cardiac arrhythmias can be crucial for timely treatment and disease progression deceleration. Certain methods for arrhythmia detection include the 12-lead electrocardiogram (ECG), a non-invasive yet spatially limited technique. For 3D mapping of the cardiac electrical conduction, electroanatomical mapping (EAM), which is ionizing, costly, and time-consuming, can be used. The EAM can only be performed invasively. Although echocardiography can be a non-invasive tool, clinical echocardiography machines operate on low frame rates of 40-80 Hz, prioritizing spatial resolution and hence, restricting the use of time-shifted based techniques such as Electromechanical Wave Imaging (EWI).

The disclosed EWI can be a non-invasive, angle-independent, higher frame rate ultrasound imaging modality that cab map the electromechanical activation of the heart, i.e., the infinitesimal mechanical response induced by the electrical activation, in all four cardiac chambers. The disclosed EWI can allow for frequency tracking of myocardial movement and strain calculation. Selection of the time-point at which the incremental strain flips from positive (relaxation) to negative (contraction), i.e., Zero Crossing (ZC), for a subset of uniformly distributed pixels can generate the EWI activation maps, referred to as EWI isochrones.

At lower FR, certain EWI strain curves can have a different profile which limits manual processing. The disclosed subject matter uses a machine learning classifier, previously trained on standard manual EWI data on canines, healthy volunteers and Wolff-Parkinson-White patients, for assisting in lower framerate EWI isochrone generation while simultaneously automating EWI processing and reducing operator bias.

Data acquisition with standard Electromechanical Wave Imaging: EWI relied on a 2-second acquisition of a single diverging wave at 2000 frames/sec, acquired on a Vantage 256 research scanner (Verasonics Inc., Kirkland, WA, USA) with a 2.5 MHz phased-array transducer (ALT P4-2, Philips, Andover, Massachusetts). Scans were performed transthoracically in 4 standard apical echocardiographic views. A 1-D cross-correlation algorithm was applied to the radiofrequency data for axial displacement estimation, followed by a least squares estimator with a 5 mm kernel for incremental axial strain calculation. For a subset of approximately 150 pixels per apical view, the electromechanical activation time or Zero Crossing of the axial strain curve was selected and displayed on an interpolated, color-coded map known as the 2D EWI isochrone expressed in milliseconds. The four 2D EWI isochrone slices are then co-registered around the LV median axis and interpolated in 3D to create the final 3D-rendered EWI isochrone. Standard manual EWI was performed on both cardiac ventricles of N=6 patients in sinus rhythm, imaged immediately post successful arrhythmia ablation. EWI results were validated with the corresponding EAM from the ablation procedure. The standard manual EWI isochrones were generated for each subject and used as the ground truth.

Automated EWI at lower frame rates: For each acquisition, the raw radiofrequency data were decimated at factors of 4, 8 and 16, resulting in acquisitions of 500 Hz, 250 Hz and 125 Hz, respectively. EWI axial strain curves were then calculated for each case using an adjusted version of the displacement estimation algorithm for the lower frame rates. Resulting strain curve features were then automatically collected for 2500 pixels per case and fed to a Random Forest Classifier (RFC) with 200 estimators or trees, trained on a standard EWI (PRF=2000 Hz) dataset, previously validated with EAM. When a single ZC is present on the axial strain curve, this constitutes a unique choice. However, when multiple ZC points exist during systole, they are referred as ZC candidates. RFC assigns a prediction probability to each ZC candidate, and therefore only 20-40% of the originally selected pixels with the highest prediction probability are chosen for automated EWI generation, excluding pixels with ZC selection of low confidence, while ensuring adequate spatial sampling. The automatically generated isochrone is inspected, and minor manual corrections are applied in areas where the ML algorithm has chosen an incorrect ZC, generating a semi-automated isochrone. For both the full and the semi-automated EWI isochrone, the 3D-rendered automated EWI isochrones were reconstructed from the predicted ZCs.

Evaluation metrics: In order to evaluate the performance of the pre-trained RFC model when applied to new test data of lower frame rate, the similarity of the automatically generated lower FR isochrones with the standard manual EWI isochrone was calculated using the following metric:

$$\text{Similarity Percentage} = \frac{\text{\# pixels with } ATD \le 20 \text{ ms}}{\text{total \# pixels}} * 100 \qquad (1)$$

with $ATD$ = absolute activation time difference =

$$|\text{activation time}(autoEWI) - \text{activation time}(manualEWI)|$$

An ATD below 20 ms is equivalent to a 10% margin of error, as the electromechanical activation is expected to happen within a 200 ms range from the ECG QRS onset, in the case of ventricular activation, or the ECG p-wave onset, in the case of atrial activation in healthy patients with no co-morbidities such as myocardial ischemia, infarction or heart failure.

Figures 11A, 11B, 11C, 11D, 11E:
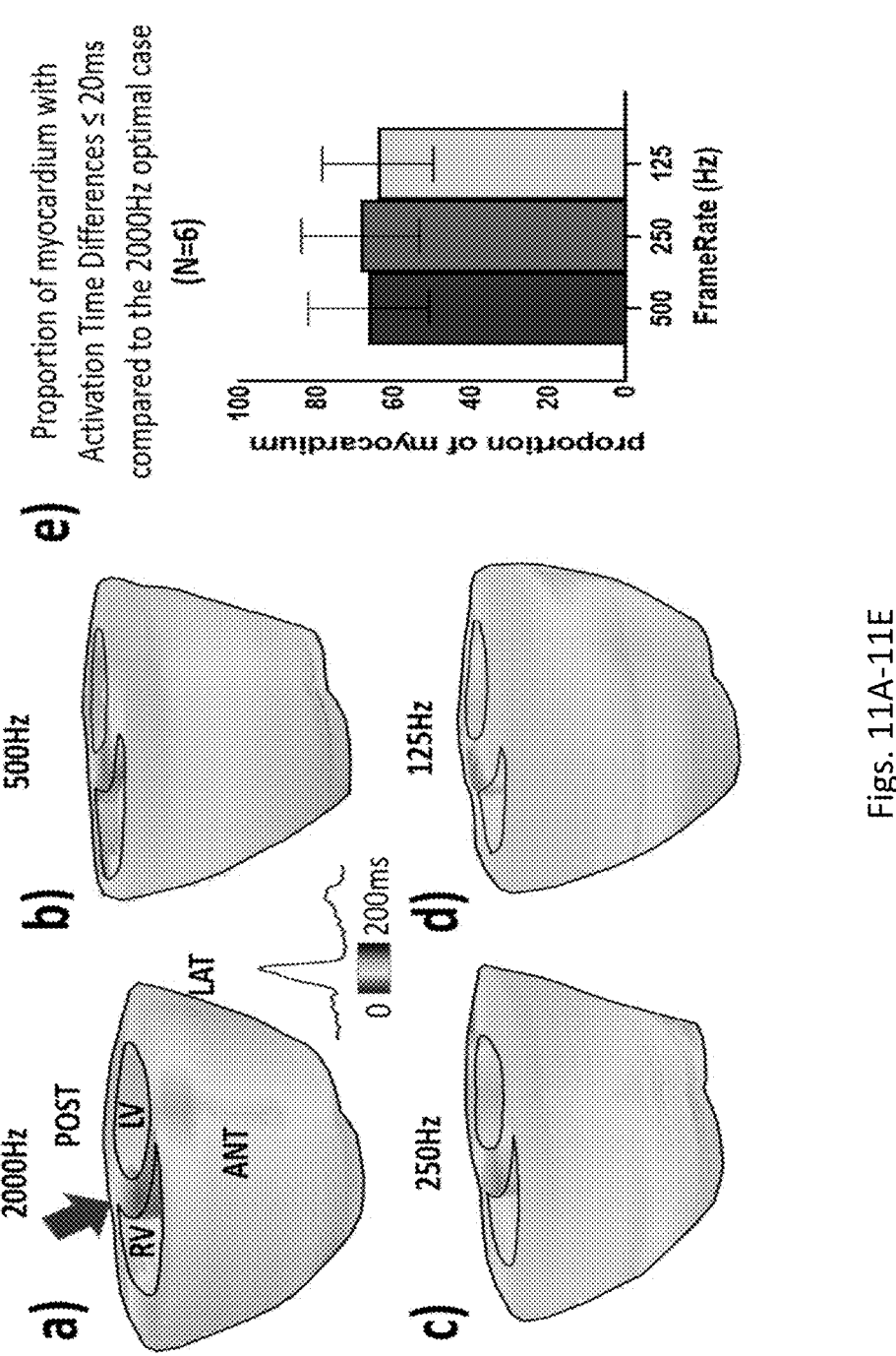
FIGS. 11A-11E provide images showing effects of EWI frame-rates on isochrone generation for the ventricles of a subject in sinus rhythm in accordance with the disclosed subject matter.

Results and discussion: RFC performance was robust in all cases (N=6), predicting correct localization of the normal early activated basal ventricular septum for all automatically generated lower frame rate EWI maps. Compared to the standard manual EWI ground truth at 2000 Hz, mean ventricular myocardial proportions of the automated maps exhibiting ATD ≤20 ms for each lower frame rate were 69%, 71% and 65% for 500 Hz, 250 Hz and 125 Hz, respectively (FIG. 11E). Overall, the propagation pattern from FIGS. 11A-11D show representative EWI maps of a 16yo male in sinus rhythm for standard manual processing and fully automated EWI results. 3D-rendered isochrones in anterior view are shown for Manual baseline at 2000 Hz (11A), Random Forest Classifier at 500 Hz (11B), 250 Hz 11C), and 125 Hz (11D). Red is the earliest activation while blue is the latest. The red arrow denotes the early activated basal septum close to the atrioventricular node. FIG. 11E shows the proportion of pixels at lower frame-rates with activation time differences of less than 20 ms, compared to the 2000 Hz baseline (N=6 patients, LV: Left Ventricle, RV: Right Ventricle, ANT: Anterior, POST: Posterior, LAT: Lateral).

The early septal activation localized during standard manual EWI (FIG. 11A) and noted with the red arrow is present in all three lower frame rates automated EWI maps (FIGS. 11B, 11C, and 11D), while, at the same time, the electromechanical activation propagation pattern throughout the rest of the myocardium shows excellent qualitative agreement. Quantitatively, the 500-Hz automated EWI maps displayed a high similarity percentage of 77% compared to the optimal manual EWI maps. Furthermore, a notable 80% and 82% similarity percentage were found for the automated EWI maps of 250 Hz and 125 Hz, respectively. The minor discrepancies that appear mostly in the LV lateral wall are insignificant and do not interfere with the correct sinus rhythm pattern detection in all 3 lower frame rate EWI maps.

Figure 12:
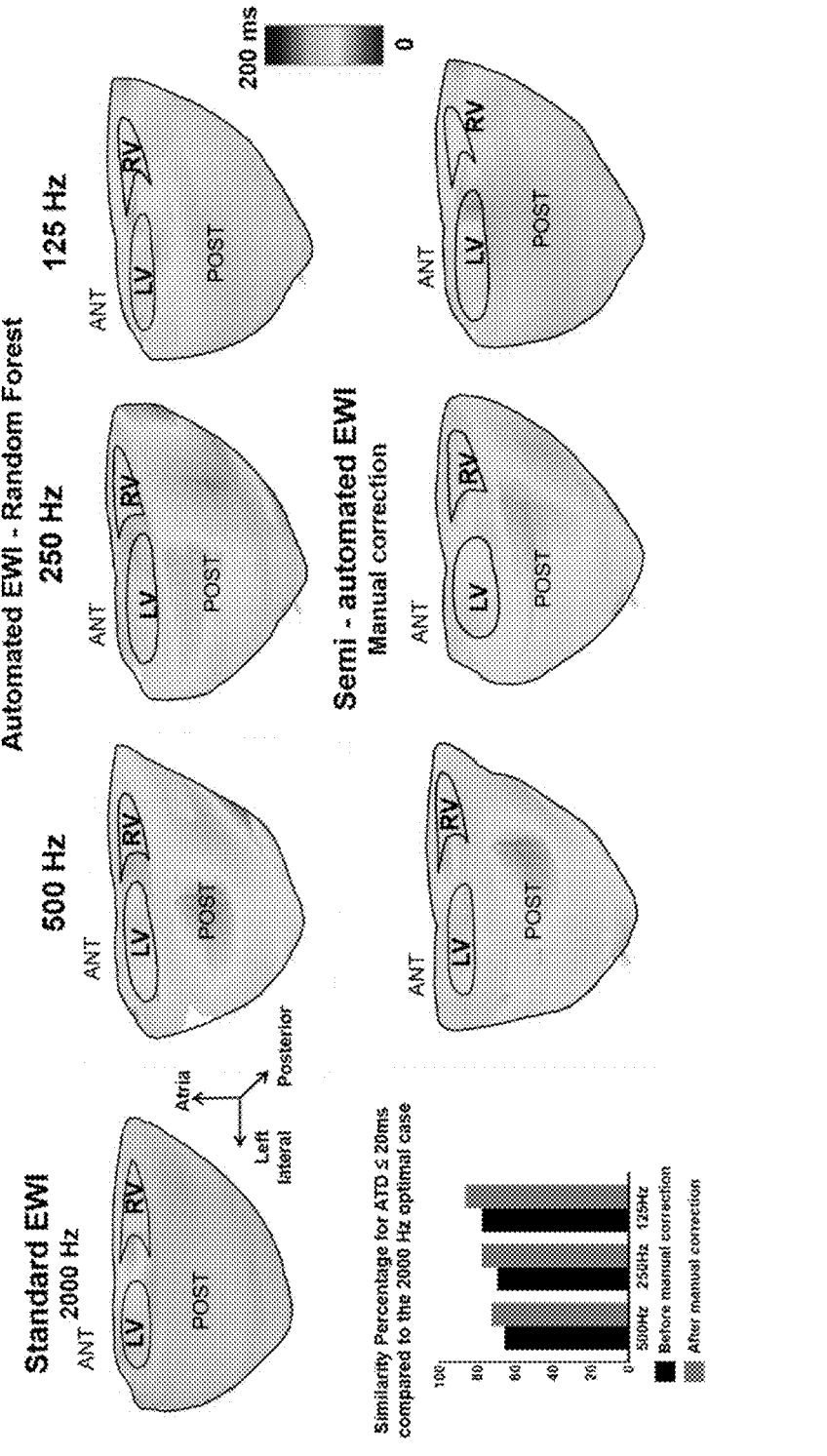
FIG. 12 provides images showing EWI manual, automated, and semi-automated isochrone maps for different frame-rates for the ventricles of a subject in sinus rhythm in accordance with the disclosed subject matter.

An example case of manual, automated and semi-automated results is depicted in FIG. 12. FIG. 12 shows EWI manual, automated and semi-automated isochrone maps for different frame-rates for the ventricles of a 54yo male in sinus rhythm. 3D-rendered isochrones in anterior view are shown for manual baseline at 2000 Hz (top left), fully automated (top) and semi-automated (bottom) Random Forest Classifier at 500 Hz, 250 Hz and 125 Hz. Red is the earliest activation, while blue is the latest. The red arrow denotes the early activated basal septum close to the atrioventricular node. The proportion of pixels at lower frame-rates with activation time differences of less than 20 ms, compared to the 2000 Hz baseline for automated and semi-automated EWI isochrones, are shown on the bottom left (N=6 patients, LV: Left Ventricle, RV: Right Ventricle, ANT: Anterior, POST: Posterior, LAT: Lateral).

The early septal activation present in the manual isochrone fails to present in the 500 Hz and 250 Hz isochrones, yet it appears in the 125 Hz. However, after manual inspection and correction, the incorrect prediction was identified, and the early activation was restored. The overall activation pattern between the manual isochrone and the semi-automated isochrones show improved qualitative and quantitative similarity, with an impressive match of the 125 Hz isochrone with the manual isochrone, showcasing an almost indistinguishable activation pattern with 92% of the myocardium activating within ms from the corresponding region in the manual isochrone. Similarity percentages are also marginally increased post-manual corrections. For reproducibility, corrections are constricted to be as limited as possible and only when deemed necessary to restore the isochrone propagation pattern from earliest to latest and limit outliers.

The disclosed subject matter can use an ML algorithm for automated and semi-automated EWI generation in lower, clinically relevant frame rates. A Random Forest Classifier, trained upon validated standard manual EWI data of 2000 Hz, was able to successfully identify the correct physiological sinus rhythm electromechanical activation pattern in N=6 patients when applied on acquisition frame rates of 500 Hz, 250 Hz and 125 Hz. Post manual correction, semi-automated reduced frame rate results exhibited excellent qualitative and quantitative agreement with original manual EWI maps. The disclosed subject matter can accelerate EWI's clinical translation and integration into clinical scanners with simultaneous automation, bringing real-time diagnostic EWI closer to the clinic.

Unless otherwise defined, all technical and scientific terms used herein have the same meaning as commonly understood by one of ordinary skill in the art. In case of conflict, the present document, including definitions, will control. Certain methods and materials are described below, although methods and materials similar or equivalent to those described herein can be used in the practice or testing of the presently disclosed subject matter. All publications, patent applications, patents, and other references mentioned herein are incorporated by reference in their entirety. The materials, methods, and examples disclosed herein are illustrative only and not intended to be limiting.

While it will become apparent that the subject matter herein described is well calculated to achieve the benefits and advantages set forth above, the presently disclosed subject matter is not to be limited in scope by the specific embodiments described herein. It will be appreciated that the disclosed subject matter is susceptible to modification, variation, and change without departing from the spirit thereof. Those skilled in the art will recognize or be able to ascertain using no more than routine experimentation, many equivalents to the specific embodiments described herein. Such equivalents are intended to be encompassed by the following claims.

What is claimed is:

1. A system for electromechanical wave imaging of a tissue of a subject, comprising:
   a transducer configured to acquire ultrasound image data of the tissue constituting a dataset, and a processor coupled to the transducer and configured to
   receive the dataset,
   perform an automated selection of at least one zero-crossing location within the dataset using a heuristic-based baseline and/or a machine learning classifier, and
   generate an electromechanical wave imaging isochrone for display on an imaging processing unit based on the automated selection.

2. The system of claim 1, wherein the machine learning classifier is selected from the group consisting of a logistic regression classifier, a support vector machine classifier, and a Random Forest classifier.

3. The system of claim 1, wherein the machine learning classifier is a Random Forest classifier, wherein the Random Forest classifier is configured to have a precision rate of more than about 89.5%.

4. The system of claim 3, wherein the Random Forest classifier includes at least about 200 estimators.

5. The system of claim 1, wherein the processor is configured to collect a plurality of features from the dataset, wherein the plurality of features includes a spatial coordinate, a positive to negative zero-crossing time-point, a slope of a strain curve at each zero-crossing location, a maximum positive strain value surrounding each zero-crossing location, a minimum negative strain value surrounding each zero-crossing location, a time-point location of the maximum and the minimum strain values, and combinations thereof.

6. The system of claim 1, wherein the machine learning classifier is trained with ground truth samples, wherein the ground truth samples are manually generated isochrones.

7. The system of claim 6, wherein the machine learning classifier is trained to select the at least one zero-crossing by
   selecting a zero-crossing location with a highest probability for each pixel, or
   selecting a zero-cross location that has a probability higher than a cutoff threshold, wherein the cutoff threshold is determined based on a sensitivity and/or true positive value of the dataset.

8. The system of claim 1, wherein the subject is a Wolff-Parkinson-White patient.

9. The system of claim 1, wherein the processor is configured to receive an external dataset and perform the automated selection based on the external dataset.

10. The system of claim 1, wherein the processor is configured to
   perform beamforming on an image acquired by the transducer,
   estimate displacement of the tissue based on the image, and
   generate an incremental strain curve based on the displacement.

11. The system of claim 1, wherein the dataset comprises electromechanical wave images, electromechanical wave imaging strain curves, or a combination thereof.

12. A method for electromechanical wave imaging of a tissue of a subject, comprising:
   acquiring, by a transduer, ultrasound image data of the tissue constituting a dataset,
   receiving by a processor, the dataset,
   performing, by the processor, an automated selection of at least one zero-crossing location using a heuristic-based baseline and/or a machine learning classifier, and
   generating, by the processor, an electromechanical wave imaging isochrone for display on an imaging processing unit, based on the automated selection.

13. The method of claim 12, wherein the machine learning classifier is selected from the group consisting of a logistic regression classifier, a support vector machine classifier, and a Random Forest classifier.

14. The method of claim 12, wherein the machine learning classifier is a Random Forest classifier, wherein the Random Forest classifier is configured to have a precision rate of more than about 89.5%.

15. The method of claim 12, further comprising collecting a plurality of features from the dataset, wherein the plurality of features includes a spatial coordinate, a positive to negative zero-crossing time-point, a slope of a strain curve at each zero-crossing location, a maximum positive strain value surrounding each zero-crossing location, a minimum negative strain value surrounding each zero-crossing location, a time-point location of the maximum and the minimum strain values, and combinations thereof.

16. The method of claim 12, further comprising training the machine learning classifier with ground truth samples, wherein the ground truth samples are manually generated isochrones.

17. The method of claim 16, wherein the machine learning classifier is trained to select the at least one zero-crossing by
   selecting a zero-crossing location with a highest probability for each pixel, or
   selecting a zero-cross location that has a probability higher than a cutoff threshold, wherein the cutoff threshold is determined based on a sensitivity and/or true positive value of a dataset.

18. The method of claim 12, wherein the subject is a Wolff-Parkinson-White patient, an Atrial Flutter patient, or a ventricular trachyacardia patient.

19. The method of claim 12, further comprising receiving an external dataset and performing the automated selection using the external dataset.

* * * * *